US009812633B2

(12) United States Patent
Minemoto et al.

(10) Patent No.: US 9,812,633 B2
(45) Date of Patent: Nov. 7, 2017

(54) PIEZOELECTRIC COMPOSITION AND METHOD FOR PRODUCING SAME, PIEZOELECTRIC ELEMENT/NON-LEAD PIEZOELECTRIC ELEMENT AND METHOD FOR PRODUCING SAME, ULTRASONIC PROBE AND DIAGNOSTIC IMAGING DEVICE

(71) Applicant: KONICA MINOLTA, INC., Chiyoda-ku, Tokyo (JP)

(72) Inventors: Hisashi Minemoto, Osaka (JP); Satoshi Wada, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 600 days.

(21) Appl. No.: 14/402,659

(22) PCT Filed: May 16, 2013

(86) PCT No.: PCT/JP2013/003130
§ 371 (c)(1),
(2) Date: Nov. 20, 2014

(87) PCT Pub. No.: WO2013/175740
PCT Pub. Date: Nov. 28, 2013

(65) Prior Publication Data
US 2015/0141834 A1 May 21, 2015

(30) Foreign Application Priority Data

May 21, 2012 (JP) .................................. 2012-115712
May 21, 2012 (JP) .................................. 2012-115713
(Continued)

(51) Int. Cl.
*H01L 41/187* (2006.01)
*H01L 41/193* (2006.01)
(Continued)

(52) U.S. Cl.
CPC ........ *H01L 41/1878* (2013.01); *A61B 8/4494* (2013.01); *C04B 35/26* (2013.01);
(Continued)

(58) Field of Classification Search
CPC ..... H01L 41/1878; H01L 41/18; H01L 41/37; H01L 41/43; A61B 8/4494; C04B 35/462; C04B 35/475; C04B 35/26
(Continued)

(56) References Cited

U.S. PATENT DOCUMENTS 8,299,688 B2   10/2012   Saito et al.
8,518,292 B2   8/2013   Saito et al.
(Continued)

FOREIGN PATENT DOCUMENTS

CN   101973763 A   2/2011
JP   2008069051 A   3/2008
(Continued)

OTHER PUBLICATIONS

Claude Ederer, et al, "Influence of strain and oxygen vacancies on the magnetoelectric properties of multiferroic bismuth ferrite", Physical Review B, 71, 2005, pp. 224103-1 to 224103-9.
(Continued)

*Primary Examiner* — Thomas Dougherty
(74) *Attorney, Agent, or Firm* — Holtz, Holtz & Volek PC

(57) ABSTRACT

The present invention is a piezoelectric composition and a piezoelectric element using the piezoelectric composition, the composition being characterized by: having a Perovskite structure represented by general formula ABO3; being represented by composition formula x(Bi0.5K0.5)TiO3-yBi(Mg0.5Ti0.5)O3-zBiFeO3, x+y+z=1 in the composition formula above; and in a triangular coordinate using x, y and z in the composition formula above, having a composition represented by a region which is surrounded by a pentagon
(Continued)

ABCDE with apexes of point A (1, 0, 0), point B (0.7, 0.3, 0), point C (0.1, 0.3, 0.6), point D (0.1, 0.1, 0.8) and point E (0.2, 0, 0.8) and which does not include the line segment AE that connects point A (1, 0, 0) and point E (0.2, 0, 0.8).

53 Claims, 17 Drawing Sheets

(30) Foreign Application Priority Data

Sep. 11, 2012 (JP) .................................. 2012-199742
Sep. 11, 2012 (JP) .................................. 2012-199743

(51) Int. Cl.
| | | |
|---|---|---|
| C04B 35/462 | (2006.01) | |
| H01L 41/43 | (2013.01) | |
| C04B 35/26 | (2006.01) | |
| C04B 35/475 | (2006.01) | |
| H01L 41/18 | (2006.01) | |
| H01L 41/37 | (2013.01) | |
| A61B 8/00 | (2006.01) | |

(52) U.S. Cl.
CPC .......... *C04B 35/462* (2013.01); *C04B 35/475* (2013.01); *H01L 41/18* (2013.01); *H01L 41/37* (2013.01); *H01L 41/43* (2013.01); *A61B 8/4444* (2013.01); *A61B 8/4483* (2013.01); *C04B 2235/3201* (2013.01); *C04B 2235/3206* (2013.01); *C04B 2235/3208* (2013.01); *C04B 2235/3234* (2013.01); *C04B 2235/3236* (2013.01); *C04B 2235/3239* (2013.01); *C04B 2235/3251* (2013.01); *C04B 2235/3258* (2013.01); *C04B 2235/3262* (2013.01); *C04B 2235/3274* (2013.01); *C04B 2235/3275* (2013.01); *C04B 2235/3279* (2013.01); *C04B 2235/3287* (2013.01); *C04B 2235/3298* (2013.01); *C04B 2235/3418* (2013.01); *Y10T 29/42* (2015.01)

(58) Field of Classification Search
USPC ....... 310/358; 252/62.9 PZ, 62.9 R; 501/134
See application file for complete search history.

(56) References Cited

U.S. PATENT DOCUMENTS

| | | | |
|---|---|---|---|
| 2013/0207020 A1 | 8/2013 | Bell et al. | |
| 2013/0270965 A1* | 10/2013 | Hayashi | B41J 2/14233 310/328 |
| 2014/0354738 A1* | 12/2014 | Yabuta | H01L 41/187 347/68 |
| 2015/0364675 A1* | 12/2015 | Wang | H01L 41/18 347/68 |

FOREIGN PATENT DOCUMENTS

| | | |
|---|---|---|
| JP | 2010126421 A | 6/2010 |
| JP | 2010235442 A | 10/2010 |
| WO | 2012013956 A1 | 2/2012 |

OTHER PUBLICATIONS

G. L. Yuan, et al, "Preparation and multi-properties of insulated single-phase BiFeO3 ceramics", Solid State Communications 138, 2006, pp. 76 to 81.

Hiroki Matsuo, et al, "Structural and piezoelectric properties of high-density (Bi0.5K0.5)TiO3—BiFeO3 ceramics", Journal of Applied Physics 108, 2010, pp. 104103-1 to 104103-6.

Ichiro Fujii, et al, "Structural, Dielectric, and Piezoelectric Properties of Mn-Doped BaTiO3—Bi(Mg1/2Ti1/2)O3—BiFeO3 Ceramics", Japanese Journal of Applied Physics 50, 2011, pp. 09ND07-1 to 09ND07-4.

International Search Report dated Jul. 2, 2013 issued in International Application No. PCT/JP2013/003130.

Tadej Rojac, et al, "Strong ferroelectric domain-wall pinning in BiFeO3 ceramics", Journal of Applied Physics 108, 2010, pp. 074107-1 to 074107-8.

Yasuhiro Yoneda, et al, "Local Structure Analysis of Bi(Mg0:5Ti0:5)O3 Grown by High Pressure Synthesis", Japanese Journal of Applied Physics 50 (2011), pp. 09NE06-1 to 09NE06-6.

Yuji Hiruma, et al, "Ferroelectric and Piezoelectric Properties of (Bi1/2K1/2)TiO3 Ceramics", Japanese Journal of Applied Physics, vol. 44, No. 7A, 2005, pp. 5040 to 5044.

* cited by examiner

PIEZOELECTRIC COMPOSITION AND METHOD FOR PRODUCING SAME, PIEZOELECTRIC ELEMENT/NON-LEAD PIEZOELECTRIC ELEMENT AND METHOD FOR PRODUCING SAME, ULTRASONIC PROBE AND DIAGNOSTIC IMAGING DEVICE

TECHNICAL FIELD

The present invention relates to a novel lead-free piezoelectric composition containing no lead. The present invention further relates to a lead-free piezoelectric element containing no lead and a method for producing the same, an ultrasonic probe including the lead-free piezoelectric element, and a diagnostic imaging apparatus including the ultrasonic probe.

BACKGROUND ART

Heretofore, various lead-free piezoelectric compositions have been studied, including, for example, $(Bi_{0.5}K_{0.5})TiO_3$ (hereinafter, also referred to as BKT) and BKT-$BiFeO_3$ (hereinafter, also $BiFeO_3$ referred to as BFO) binary lead-free piezoelectric compositions. Their piezoelectric constants, however, are still small compared with those of lead-based piezoelectric compositions under the present circumstances (see, for example, PTL 1 and PTL 2 and NPL 1 and NPL 2). In addition, a solid solution of BKT and $Bi(Fe,Co)O_3$ (hereinafter, also referred to as BFCO) which is derived from $BiFeO_3$ by the replacement of Fe with Co is just beginning to be studied (for example, PTL 3). On the other hand, a complex oxide $Bi(Mg_{0.5}Ti_{0.5})O_3$ (hereinafter, also referred to as BMT) is known as a composition that is difficult to synthesize at normal pressure and yields a single phase only at high temperature and high pressure, and this hard-to-prepare composition is also known to be so unstable that the composition, even once prepared, is decomposed at hundreds of ° C. at normal pressure (for example, NPL 3). For this reason, conventional lead-free piezoelectrics have been little studied as to their combination with a $BaTiO_3$ (hereinafter, also referred to as BT) system (see, for example, PTL 4 and NPL 6), but have not been studied as to their application to a BKT-BFO system.

Lead-free piezoelectric elements including a BFO-based piezoelectric composition presumably have a large spontaneous polarization (approximately 100 $\mu C/cm^2$) (NPL 4) and thus, have been studied actively in recent years. According to the report, however, such piezoelectric compositions having a large spontaneous polarization are difficult to actually obtain on the grounds that, for example, leak current is large and pinning hinders the spontaneous polarization from appearing (NPL 5). Various solutions thereto have been proposed, including, for example, a method involving sintering from very fine starting materials (PTL 1 and NPL 2), a method involving dipping in hot water starting at high temperature, followed by quenching at a very fast rate (NPL 5 and NPL 6), a method involving temperature elevation at a rate as fast as 100° C./second (in order to suppress the evaporation of a highly volatile element such as Bi), followed by sintering in a short time (NPL 7), and a method involving sintering at a temperature near the melting point of a piezoelectric composition to prepare a closely packed sintered body, thereby improving the properties of a lead-free piezoelectric element (PTL 2). Also, a BFO-based lead-free piezoelectric ceramic rich in Co in addition to Fe has been reported (PTL 3).

CITATION LIST

Patent Literature

PTL 1
Japanese Patent Application Laid-Open No. 2008-69051
PTL 2
Japanese Patent Application Laid-Open No. 2010-126421
PTL 3
WO2012/013956
PTL 4
Japanese Patent Application Laid-Open No. 2010-235442

Non-Patent Literature

NPL 1
Japanese Journal of Applied Physics, Vol. 44, No. 7A, pp. 5040-5044 (2005)
NPL 2
Journal of Applied Physics, Vol. 108, 104103 (2010)
NPL 3
Japanese Journal of Applied Physics, Vol. 50, 09NE06 (2011)
NPL 4
C. Ederer et al., Phys. Rev. B, 71 224103 (2005)
NPL 5
Journal of Applied Physics, Vol. 108, 074107 (2010)
NPL 6
Japanese Journal of Applied Physics, Vol. 50, 09ND07 (2011)
NPL 7
G. L. Yuan et al., Solid State communication, Vol. 138, pp. 76-81 (2006)

SUMMARY OF INVENTION

Technical Problem

As mentioned above, BKT alone fails to yield a piezoelectric composition having a sufficiently large piezoelectric constant. BKT alone or BKT-BFO is difficult to sinter and thus requires using a nanopowder synthesized from a vapor phase, as a starting material (PTL 1 and NPL 2). Moreover BKT-BFCO or the like unfortunately fails to exert great piezoelectric performance with high reproducibility due to large leak current or because spontaneous polarization or remnant polarization is subject to pinning by various defects.

Lead-free piezoelectric elements including the aforementioned BFO-based piezoelectric composition present the following problems: defects such as Bi vacancy or oxygen vacancy are increased, because the amount of highly volatile Bi increases with an increase in the amount of BFO. In addition, a large spontaneous polarization or remnant polarization cannot be obtained in an electric field-polarization curve, because domains or domain walls are pinned by various defects or defect pairs. Moreover, high voltage cannot be applied to the elements, because the influence of oxygen vacancy or the like changes the valence of Fe from $Fe^{3+}$ to $Fe^{2+}$ to increase the leak current of the elements. As a result, disadvantageously, originally expected ferroelectricity or piezoelectric properties cannot be obtained (for example, NPL 5). Alternatively, the lead-free piezoelectric ceramic described in PTL 3, which is rich in Co in addition to Fe, unfortunately fails to exert great piezoelectric properties with high reproducibility due to larger leak current or because domains or domain walls are pinned by defects, etc.

An object of the present invention is to solve the problems mentioned above and to provide a lead-free piezoelectric composition and a lead-free piezoelectric element having a large piezoelectric constant with high reproducibility by a convenient process.

Solution to Problem

According to a first aspect, a piezoelectric composition is a piezoelectric composition having a perovskite structure represented by general formula $ABO_3$ and having a composition represented by compositional formula $x(Bi_{0.5}K_{0.5})TiO_3\text{-}yBi(Mg_{0.5}Ti_{0.5})O_3\text{-}zBiFeO_3$, in which $x+y+z=1$, and also represented by a region, in triangle coordinates using x, y, and z in the compositional formula, enclosed by pentagon ABCDE with vertices of point A (1,0,0), point B (0.7,0.3,0), point C (0.1,0.3,0.6), point D (0.1,0.1,0.8), and point E (0.2,0,0.8) but exclusive of segment AE joining point A (1,0,0) and point E (0.2,0,0.8).

According to a first aspect, a first method for producing a piezoelectric composition is a method for producing the aforementioned piezoelectric composition of the first aspect, including a starting material preparation step, a temperature elevation step, a heat treatment step, and a cooling step in the order presented.

According to a first aspect, a second method for producing a piezoelectric composition is a method for producing the aforementioned piezoelectric composition of the first aspect, including a starting material preparation step, a temperature elevation step, a first heat treatment step, a temperature lowering step, a second heat treatment step, and a cooling step in the order presented.

According to a first aspect, a third method for producing a piezoelectric composition is a method for producing the aforementioned piezoelectric composition of the first aspect, including a starting material preparation step, a first temperature elevation step, a first heat treatment step, a first cooling step, a second temperature elevation step, a second heat treatment step, and a second cooling step in the order presented.

According to a first aspect, a piezoelectric element includes the aforementioned piezoelectric composition of the first aspect and an electrode that applies voltage to the piezoelectric composition.

According to a second aspect, a lead-free piezoelectric element is a lead-free piezoelectric element including a piezoelectric composition and an electrode that applies voltage to the piezoelectric composition, the piezoelectric composition having a perovskite structure represented by general compositional formula $ABO_3$ and containing $BiFeO_3$ and a Bi complex oxide, the $BiFeO_3$ having a content of 3 to 80 mol % with respect to the whole piezoelectric composition, and the Bi complex oxide containing, in the general compositional formula, Bi at site A and a plurality of elements differing in valence at site B, in which the lead-free piezoelectric element has a relative permittivity $\in r$ of 400 or larger and a dielectric loss $\tan \delta$ of 0.2 or smaller at 25° C., and has a piezoelectric constant d33* of 250 pm/V or higher determined from an electric field-strain curve.

According to a second aspect, an ultrasonic probe includes the aforementioned lead-free piezoelectric element of the second aspect.

According to a second aspect, a diagnostic imaging apparatus includes the aforementioned ultrasonic probe of the second aspect.

According to a second aspect, a first method for producing a lead-free piezoelectric element is a method for producing the aforementioned lead-free piezoelectric element of the second aspect, including a starting material preparation step, a temperature elevation step, a first heat treatment step, a temperature lowering step, a second heat treatment step, and a cooling step in the order presented to produce a piezoelectric composition contained in the lead-free piezoelectric element.

According to a second aspect, a second method for producing a lead-free piezoelectric element is a method for producing the aforementioned lead-free piezoelectric element of the second aspect, including a starting material preparation step, a first temperature elevation step, a first heat treatment step, a first cooling step, a second temperature elevation step, a second heat treatment step, and a second cooling step in the order presented to produce a piezoelectric composition contained in the lead-free piezoelectric element.

Advantageous Effects of Invention

According to a first aspect, the present invention can provide a piezoelectric composition having a larger piezoelectric constant than that of each of BKT alone, BMT alone (which is difficult to synthesize at normal pressure), and BFO alone. In addition, BKT-BMT-BFO complex composition provides a convenient way to produce a piezoelectric composition.

According to a second aspect, the present invention can provide a lead-free piezoelectric element including a BFO-based piezoelectric composition and having a large spontaneous polarization or remnant polarization, small leak current, and high piezoelectric properties, and a method for producing the same.

DESCRIPTION OF EMBODIMENTS

First Aspect

Hereinafter, the first aspect will be described.

Embodiment 1-1

First, the piezoelectric composition of the first aspect will be described.

The piezoelectric composition of the first aspect has a perovskite structure represented by general formula $ABO_3$ and is represented by compositional formula $x(Bi_{0.5}K_{0.5})TiO_3$-$yBi(Mg_{0.5}Ti_{0.5})O_3$-$zBiFeO_3$. In the compositional formula, $x+y+z=1$. The piezoelectric composition has a composition represented by a region, in triangle coordinates using x, y, and z in the compositional formula, enclosed by pentagon ABCDE with vertices of point A (1,0,0), point B (0.7,0.3,0), point C (0.1,0.3,0.6), point D (0.1,0.1,0.8), and point E (0.2,0,0.8) but exclusive of segment AE joining point A (1,0,0) and point E (0.2,0,0.8).

The BKT-BMT-BFO complex composition can yield a piezoelectric composition having a larger piezoelectric constant than that of each of BKT alone, BMT alone, and BFO alone, and provides a convenient way to produce this piezoelectric composition.

Figure 1:
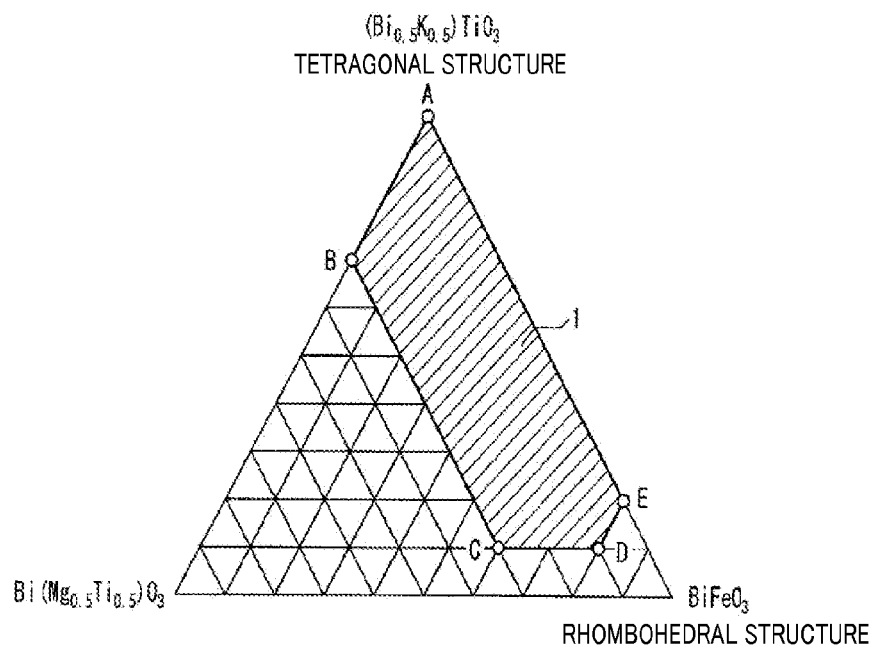
FIG. 1 illustrates triangle coordinates that define a composition region of the piezoelectric composition of the first aspect.

FIG. 1 illustrates composition region 1 that is enclosed by pentagon ABCDE with vertices of point A (1,0,0), point B (0.7,0.3,0), point C (0.1,0.3,0.6), point D (0.1,0.1,0.8), and point E (0.2,0,0.8) in triangle coordinates using x, y, and z in the compositional formula. However, the composition region according to the first aspect is exclusive of segment AE joining point A (1,0,0) and point E (0.2,0,0.8).

Starting materials for the piezoelectric composition indicated by composition region 1 can be relatively easily sintered, and the piezoelectric composition indicated by composition region 1 has a large piezoelectric constant d33* determined from the maximum slope of electric field-strain properties.

On the other hand, a composition with an amount of BFO exceeding 0.8 (composition with z>0.8) is not preferred because such composition increases leak current or emphasizes a phenomenon in which domain movement is pinned; thus the resulting piezoelectric composition does not exhibit great piezoelectric properties.

In the case of z=0, the composition of the first aspect is indicated by segment AB joining point A (1,0,0) and point B (0.7,0.3,0) but exclusive of point A (1,0,0). The composition is exclusive of point A (1,0,0) because y=z=0 at point A yields a composition consisting of BKT alone, resulting in a not much large value of d33* and remarkably strict sintering conditions during production. For example, BKT alone can be sintered at approximately 1,060° C. By contrast, a temperature a few ° C. lower than the temperature cannot improve sintered density, whereas a temperature a few ° C. higher than the temperature partially melts starting materials. Thus, the optimum range of sintering temperatures for producing the piezoelectric composition becomes narrower, and sintering is thus rendered difficult. The present inventors have found that the dissolution of BMT or BMT-BFO in BKT remarkably facilitates sintering.

A composition with an amount of BMT exceeding 0.3 (composition with y>0.3) often generates a heterogeneous phase other than the perovskite structure or decreases a piezoelectric constant d33*. A composition with an amount of BMT less than 0.02 (composition with y<0.02) is disadvantageously too similar to the composition of BKT-BFO to achieve sintering, as in BKT-BFO.

Next, more preferred forms of the piezoelectric composition of the first aspect will be described.

BKT has a tetragonal structure, and BFO has a rhombohedral structure. Thus, a phase boundary exists between these structures. In this context, the phase boundary refers to a composition region in which at least 2 types of crystal structures coexist with each other. In conventional approaches, BMT can be produced only under conditions of high temperature and high pressure and as such, may also be difficult to produce as a solid solution. Combination BKT-BMT or BKT-BMT-BFO has not yet been studied. Thus, its phase boundary has also been totally unknown. The present inventors have revealed for the first time that a tetragonal-pseudocubic phase boundary and a rhombohedral-pseudocubic phase boundary also exist in a BKT-BMT-BFO solid solution composition. The present inventors have further found for the first time that, in proximity to the phase boundary, a piezoelectric composition having drastically great piezoelectric properties compared with those of a piezoelectric composition produced by a usual method can be achieved by annealing treatment or relatively rapid air cooling, as shown later in a method for producing the piezoelectric composition of the first aspect.

Specifically, the piezoelectric composition of the first aspect preferably has a composition represented by a region, in the triangle coordinates, enclosed by pentagon AFGHI with vertices of point A (1,0,0), point F (0.8,0.2,0), point G (0.7,0.2,0.1), point H (0.7,0.1,0.2), and point I (0.8,0,0.2) but exclusive of segment AI joining point A (1,0,0) and point I (0.8,0,0.2). More preferably, the piezoelectric composition of the first aspect has a composition including a tetragonal-pseudocubic phase boundary or a composition located in proximity to the phase boundary.

Alternatively, the piezoelectric composition of the first aspect preferably has a composition represented by a region, in the triangle coordinates, enclosed by pentagon JKLMN with vertices of point J (0.6,0,0.4), point K (0.5,0.2,0.3), point L (0.2,0.2,0.6), point M (0.2,0.1,0.7), and point N (0.3,0,0.7) but exclusive of segment JN joining point J (0.6,0,0.4) and point N (0.3,0,0.7). More preferably, the piezoelectric composition of the first aspect has a composition including a rhombohedral-pseudocubic phase boundary or a composition located in proximity to the phase boundary.

Figure 2:
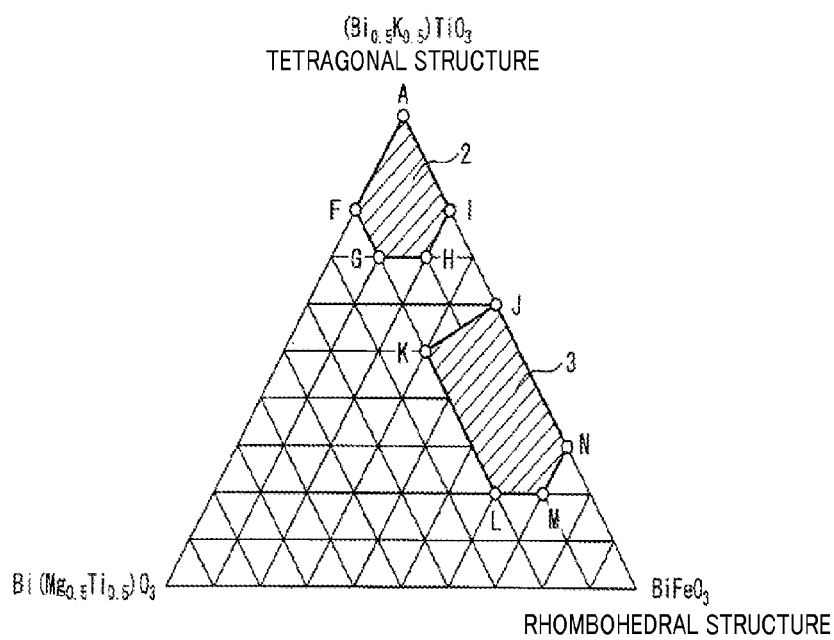
FIG. 2 illustrates triangle coordinates that define a more preferred composition region of the piezoelectric composition of the first aspect.

FIG. 2 illustrates composition region 2 that is enclosed by pentagon AFGHI with vertices of point A (1,0,0), point F (0.8,0.2,0), point G (0.7,0.2,0.1), point H (0.7,0.1,0.2), and point I (0.8,0,0.2) in the triangle coordinates, and composition region 3 that is enclosed by pentagon JKLMN with vertices of point J (0.6,0,0.4), point K (0.5,0.2,0.3), point L (0.2,0.2,0.6), point M (0.2,0.1,0.7), and point N (0.3,0,0.7) in the triangle coordinates. However, composition region 2 according to the first aspect is exclusive of segment AI joining point A (1,0,0) and point I (0.8,0,0.2), and composition region 3 according to the first aspect is exclusive of segment JN joining point J (0.6,0,0.4) and point N (0.3,0, 0.7).

The piezoelectric composition of the first aspect has a perovskite structure which is represented by general compositional formula $ABO_3$. The standard molar ratio of the site-A element, the site-B element, and oxygen is 1:1:3. The molar ratio of these moieties may fall outside the standard molar ratio within a range that can form the perovskite structure.

For the piezoelectric composition of the first aspect, Mg in the compositional formula is preferably partially replaced with Zn, and Bi in the compositional formula is preferably partially replaced with at least one type selected from La, Sm, and Nd. Furthermore, Ti in the compositional formula is preferably partially replaced with Zr. The replacement of these elements can lower curie temperature (Tc) or maximum temperature (Tm) of permittivity. Tc (or Tm) thus lowered can be expected to produce a large piezoelectric constant and a large permittivity in the piezoelectric composition of the first aspect that exhibits relaxor properties.

Preferably, the piezoelectric composition of the first aspect further contains 2 wt % or less of at least one element selected from the group consisting of Mn, Co, Ni, V, Nb, Ta, W, Si, Ge, Ca, and Sr. Mn, Co, Ni, or V thus contained therein can bring the changed valence of Fe back to trivalence and can be expected to reduce leak current. Since Nb, Ta, V, or W makes a contribution as a donor, these elements thus contained therein can be expected to soften materials. Si or Ge thus contained therein can be expected to improve sintered density and to improve an electromechanical coupling coefficient. Sr or Ca thus contained therein can be expected to reduce the evaporation of Bi or K and consequently, can improve properties or reliability.

At least one element selected from the group consisting of Mn, Co, Ni, V, Nb, Ta, W, Si, Ge, Ca, and Sr mentioned above does not have to be dissolved in the crystal of the piezoelectric composition and may be deposited in crystal grains or grain boundary or may be segregated.

Embodiment 1-2

Next, a method for producing the piezoelectric composition of the first aspect will be described with reference to the accompanying drawings. The production method given below can conveniently produce the piezoelectric composition described above in Embodiment 1-1.

[First Production Method]

Figure 3:
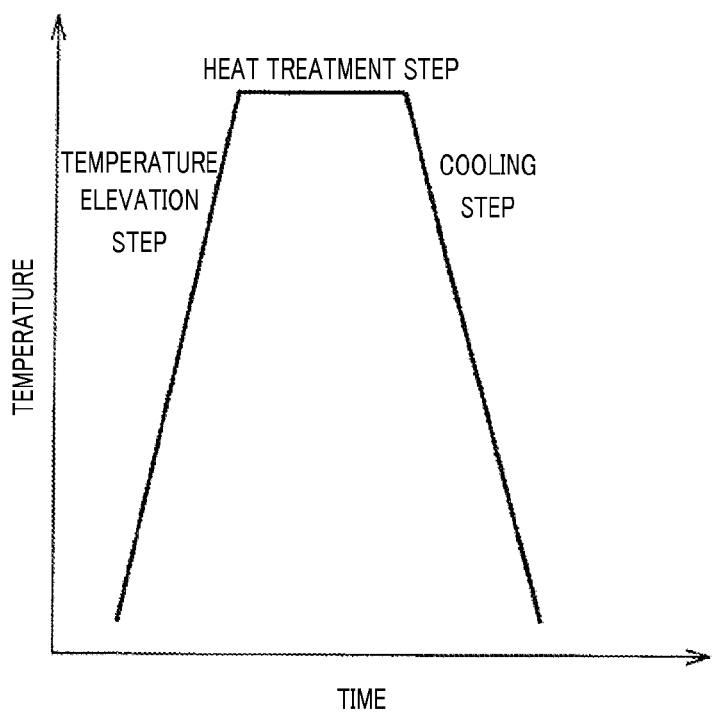
FIG. 3 schematically illustrates a first method for producing the piezoelectric composition of the first aspect except for a starting material preparation step.

FIG. 3 schematically illustrates a first method for producing the piezoelectric composition of the first aspect except for a starting material preparation step. The first method for producing the piezoelectric composition of the first aspect includes a starting material preparation step, a temperature elevation step, a heat treatment step, and a cooling step in the order presented.

<Starting Material Preparation Step>

First, oxide, carbonate, bicarbonate, various acid salts, or the like of each element constituting the piezoelectric composition of the first aspect is prepared as a starting material.

For example, $Bi_2O_3$, $Fe_2O_3$, $TiO_2$, and $MgO$ can be used as oxides. Also, $K_2CO_3$ or $KHCO_3$ can be used as carbonate.

As mentioned above, $K_2CO_3$ or $KHCO_3$ can be used as a potassium source for the piezoelectric composition of the first aspect. Preferably, $KHCO_3$ is used. This is because $KHCO_3$ has much smaller hygroscopicity than that of $K_2CO_3$ and can therefore reduce weighing errors as a starting material.

Next, a mixture of starting material powders is prepared using necessary amounts of weighed starting materials. The method for preparing the mixture can be any of dry and wet methods. Wet grinding using, for example, a ball mill or a jet mill can be appropriately used. In the case of performing the wet grinding using a ball mill, the starting materials are mixed with a dispersion medium, and this mixture is added to a grinding apparatus. Any of various alcoholic materials (e.g., methanol and ethanol), any of various organic liquids, or pure water can be used as the dispersion medium. Since water-soluble $K_2CO_3$ or $KHCO_3$ is used as a starting material, an alcoholic material is desirable from the viewpoint of liquid waste disposal or the absence of water. A grinding medium such as zirconia balls or alumina balls is further added to the grinding apparatus where mixing and grinding are then carried out until the grain size of the starting materials becomes fine and uniform. Next, the grinding medium is removed, and the dispersion medium is removed by use of suction filtration or a dryer. Then, the obtained starting material powders are placed in a container such as a crucible, followed by preliminary firing. The preliminary firing can be carried out at a temperature of, for example, 600 to 1,000° C. This can achieve homogeneous composition of the mixture and improvement in sintered density after sintering. However, the preliminary firing is not necessarily required. Instead, a compact preparation step mentioned below may be carried out using the starting material powders from which the dispersion medium has been removed by drying. On the other hand, the preliminary firing may be performed twice or more in order to improve homogeneity or sintered density.

In the case of performing the preliminary firing, preliminarily fired powders after the preliminary firing are ground again in the same way as in the grinding of the starting material powders using a grinding apparatus. In the grinding step following the preliminary firing, a binder or the like is added thereto at any of initial, intermediate, and final stages, followed by drying again to prepare starting material powders. For example, polyvinyl alcohol (PVA) or polyvinyl butyral (PVB) can be used as the binder.

Next, the obtained mixed powder of organic components and a ceramic is formed into cylindrical pellets of approximately 10 mm in diameter and approximately 1 mm in thickness to approximately 50 mm in diameter and approximately 5 mm in thickness using, for example, a press machine. Finally, the obtained compact is placed in an electric furnace and heated at 500 to 750° C. for a few hours to approximately 20 hours for binder removal treatment to obtain a starting material compact.

The starting material preparation step is described above with reference to the usual solid-phase method. However, the starting material preparation step is not limited by the solid-phase method and may be carried out by, for example, a hydrothermal synthesis method or a method using alkoxide as a starting material.

<Temperature Elevation Step>

Next, as illustrated in FIG. 3, the obtained starting material compact is placed again in a crucible or the like, and the temperature is elevated to the temperature of the heat treatment step. The rate of temperature rise is usually set to 50 to 300° C./hr, though differing depending on the size of the starting material compact. For the purpose of removing water, for example, the temperature may be kept at 100 to 200° C. for a given time, or the rate of temperature rise may be slowed down. Such cases are also included in the temperature elevation step of the first aspect.

<Heat Treatment Step>

Next, as illustrated in FIG. 3, the starting material compact is heat-treated at 900 to 1,080° C. for 5 minutes to 4 hours.

<Cooling Step>

Finally, as illustrated in FIG. 3, the compact thus heat-treated is cooled to room temperature. This cooling step is carried out in order to prevent various defects of the piezoelectric composition from gathering at domain walls. The rate of cooling is preferably 0.01 to 200° C./second, more preferably 5 to 100° C./second. A rate of cooling of 200° C./second or slower can be on the order of 1/10 to 1/100 or less of the rate of cooling in, for example, ultrahigh-speed quenching from a temperature of 800° C. by dipping in hot water of 70° C. and thus, can avoid destroying the piezoelectric composition.

[Second Production Method]

Figure 4:
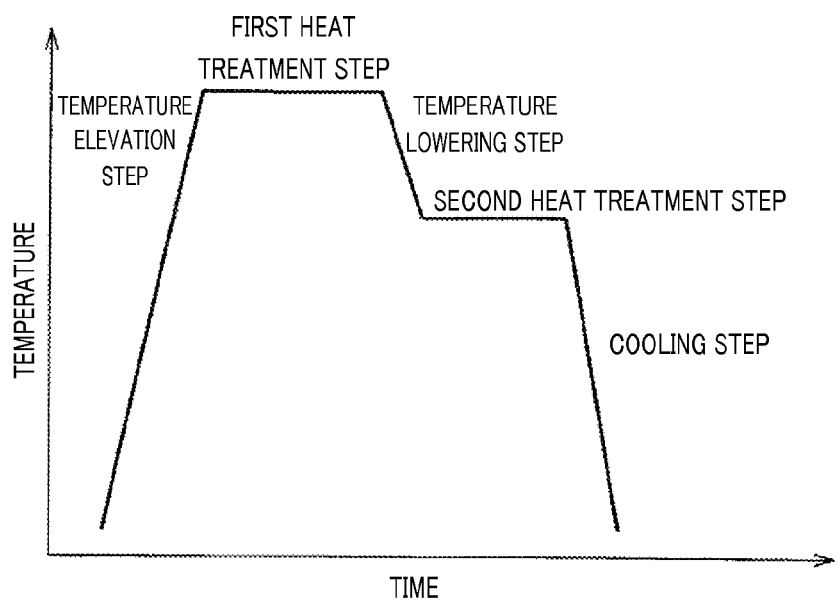
FIG. 4 schematically illustrates a second method for producing the piezoelectric composition of the first aspect except for a starting material preparation step.

FIG. 4 schematically illustrates a second method for producing the piezoelectric composition of the first aspect except for a starting material preparation step. The second method for producing the piezoelectric composition of the first aspect includes a starting material preparation step, a temperature elevation step, a first heat treatment step, a temperature lowering step, a second heat treatment step, and a cooling step in the order presented.

<Starting Material Preparation Step>

The starting material preparation step in the second production method is carried out in the same way as in the starting material preparation step in the first production method.

<Temperature Elevation Step>

As illustrated in FIG. 4, the temperature elevation step in the second production method is carried out in the same way as in the temperature elevation step in the first production method.

<First Heat Treatment Step>

Next, as illustrated in FIG. 4, the starting material compact is heat-treated at 900 to 1,080° C. When the piezoelectric composition of interest is a ceramic, the heat treatment time is 2 to 300 hours, more preferably 6 to 200 hours. In the case of obtaining a ceramic as the piezoelectric composition, this first heat treatment step serves as a sintering step for the starting material compact. This heat treatment time can be controlled to thereby control the particle size of the ceramic. The ceramic obtained as the piezoelectric composition has a particle size of preferably 0.5 to 200 μm, more preferably 1 to 100 μm. This preferred particle size of the piezoelectric composition can be achieved by the heat treatment time (sintering time) set to 6 to 300 hours.

When the piezoelectric composition of interest is a single crystal, the heat treatment temperature is 6 to 3,000 hours. In the case of obtaining a single crystal as the piezoelectric composition, this first heat treatment step serves as a crystal growth step for the starting material compact.

<Temperature Lowering Step>

As mentioned later, the second heat treatment step serves as an annealing step. As illustrated in FIG. 4, the temperature lowering step therefore intervenes between the first heat treatment step and the second heat treatment step. The rate of temperature drop is not particularly limited and can be set to 50 to 1,000° C./hr for the ceramic and to 0.1 to 200° C./hr for the single crystal.

<Second Heat Treatment Step>

Next, as illustrated in FIG. 4, the second heat treatment step is carried out for the starting material compact. This second heat treatment step serves as an annealing step. The annealing temperature is set to 300 to 900° C., more preferably 400 to 800° C. The annealing time is set to 5 minutes to 100 hours. This annealing step is carried out in order to remove various defects of the piezoelectric composition.

Also preferably, the annealing step is carried out in two or more rounds at different temperatures respectively. This is because various defects are removed at temperatures that are not the same among the defects.

<Cooling Step>

As illustrated in FIG. 4, the cooling step in the second production method is carried out in the same way as in the cooling step in the first production method.

[Third Production Method]

Figure 5:
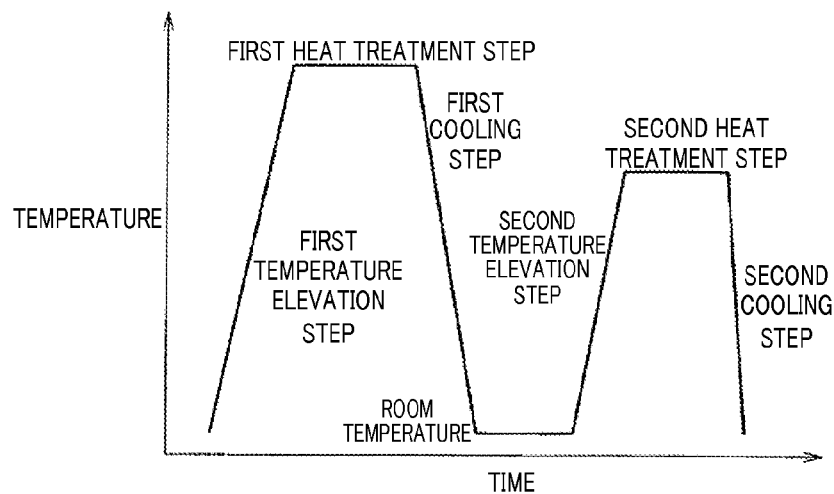
FIG. 5 schematically illustrates a third method for producing the piezoelectric composition of the first aspect except for a starting material preparation step.

FIG. 5 schematically illustrates a third method for producing the piezoelectric composition of the first aspect except for a starting material preparation step. The third method for producing the piezoelectric composition of the first aspect includes a starting material preparation step, a first temperature elevation step, a first heat treatment step, a first cooling step, a second temperature elevation step, a second heat treatment step, and a second cooling step in the order presented.

<Starting Material Preparation Step>

The starting material preparation step in the third production method is carried out in the same way as in the starting material preparation step in the first production method.

<First Temperature Elevation Step>

As illustrated in FIG. 5, the first temperature elevation step in the third production method is carried out in the same way as in the temperature elevation step in the first production method.

<First Heat Treatment Step>

As illustrated in FIG. 5, the first heat treatment step in the third production method is carried out in the same way as in the first heat treatment step in the second production method.

<First Cooling Step>

Next, as illustrated in FIG. 5, the compact thus heat-treated is cooled to room temperature. The first cooling step can be carried out at substantially the same rate of cooling as that in the cooling step in the first production method. Although not shown in FIG. 5, the step of processing the compact after the first cooling step into a compact having a smaller shape may be additionally carried out. This enables the second heat treatment step (annealing step) mentioned later to be carried out for the compact having a smaller shape and consequently, can reliably prevent the piezoelectric composition from being destroyed by thermal shock in the second cooling step mentioned later.

<Second Temperature Elevation Step>

As mentioned later, the second heat treatment step serves as an annealing step. As illustrated in FIG. 5, the temperature elevation step is therefore carried out after the first cooling step. The rate of temperature rise is not particularly limited and can be set to 50 to 1,000° C./hr.

<Second Heat Treatment Step>

As illustrated in FIG. 5, the second heat treatment step in the third production method is carried out in the same way as in the second heat treatment step in the second production method.

<Second Cooling Step>

As illustrated in FIG. 5, the second cooling step in the third production method is carried out in the same way as in the cooling step in the second production method.

Embodiment 1-3

Figure 6:
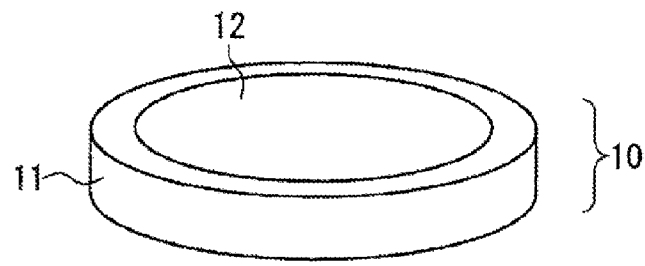
FIG. 6 is a perspective view illustrating one example of the piezoelectric element of the first aspect.

Next, the piezoelectric element of the first aspect will be described with reference to the accompanying drawings. FIG. 6 is a perspective view illustrating one example of the piezoelectric element of the first aspect. The piezoelectric element of the first aspect includes the piezoelectric composition described above in Embodiment 1-1 and an electrode that applies voltage to the piezoelectric composition. Specifically, as illustrated in FIG. 6, piezoelectric element 10 of the first aspect includes piezoelectric composition 11 and electrode 12 that applies voltage to piezoelectric composition 11.

The piezoelectric element of the first aspect has a piezoelectric constant d33* of preferably 140 pm/V or higher, more preferably 200 pm/V or higher, most preferably 250 pm/V or higher, determined from an electric field-strain curve.

Hereinafter, the first aspect will be described with reference to Examples. In Examples shown below, a bulk ceramic was used as a piezoelectric composition. However, the form of the piezoelectric composition of the first aspect is not limited to a ceramic, and the piezoelectric composition of the first aspect may be in the form of an oriented ceramic, a thick film, or a single crystal.

First, Examples based on the first method for producing the piezoelectric composition of the first aspect will be described.

Example 1-1

Starting Material Preparation Step 30 g in total of $Bi_2O_3$, $KHCO_3$, $TiO_2$, and MgO was weighed such that the composition of the resulting piezoelectric composition satisfied compositional formula 0.95 $(Bi_{0.5}K_{0.5})TiO_3$-0.05$Bi(Mg_{0.5}Ti_{0.5})O_3$ [x=0.95, y=0.05, and z=0] to prepare starting materials. Next, the weighed starting materials were placed in a pot together with ethanol and zirconia balls and ground for 16 hours using a ball mill. Then, the starting materials were dried. The starting material powders were further preliminarily fired at 800° C. for 6 hours. The obtained starting material powders were placed again in a pot together with ethanol and zirconia balls and ground again for 16 hours using a ball mill. Then, PVB was added thereto as a binder, followed by drying. Next, a pressure of approximately 200 to 250 MPa was applied to the obtained starting material powders using a uniaxial press apparatus to prepare pellets of 10 mm in diameter and 1.5 mm in thickness. The obtained pellets were heated at 700° C. for 10 hours for removal of the binder to obtain a starting material compact.

<Temperature Elevation Step>

Next, the temperature of the obtained starting material compact was elevated to 1,060° C. at a rate of temperature rise of 300° C./hr.

<Heat Treatment Step>

Subsequently, the starting material compact was sintered at 1,060° C. for 2 hours.

<Cooling Step>

Finally, the compact thus sintered was cooled to room temperature at a rate of cooling of 1,060° C./5 hours (0.058° C./second) to obtain a piezoelectric composition.

Next, the obtained piezoelectric composition was processed into a thickness of approximately 0.4 mm by polishing. Then, gold electrodes were formed on both sides of the piezoelectric composition by sputtering to obtain a piezoelectric element.

Example 1-2

A piezoelectric composition and a piezoelectric element were produced in the same way as in Example 1-1 except that: the starting materials used were 30 g in total of $Bi_2O_3$, $KHCO_3$, $TiO_2$, and MgO weighed such that the composition of the piezoelectric composition satisfied compositional formula $0.9(Bi_{0.5}K_{0.5})TiO_3$-$0.1Bi(Mg_{0.5}Ti_{0.5})O_3$ [x=0.9, y=0.1, and z=0]; and the sintering temperature was set to 1,070° C.

Example 1-3

A piezoelectric composition and a piezoelectric element were produced in the same way as in Example 1-1 except that: the starting materials used were 30 g in total of $Bi_2O_3$, $KHCO_3$, $TiO_2$, and MgO weighed such that the composition of the piezoelectric composition satisfied compositional formula $0.85(Bi_{0.5}K_{0.5})TiO_3$-$0.15Bi(Mg_{0.5}Ti_{0.5})O_3$ [x=0.85, y=0.15, and z=0]; and the sintering temperature was set to 1,080° C.

Example 1-4

A piezoelectric composition and a piezoelectric element were produced in the same way as in Example 1-1 except that: the starting materials used were 30 g in total of $Bi_2O_3$, $KHCO_3$, $TiO_2$, and MgO weighed such that the composition of the piezoelectric composition satisfied compositional formula $0.8(Bi_{0.5}K_{0.5})TiO_3$-$0.2Bi(Mg_{0.5}Ti_{0.5})O_3$ [x=0.8, y=0.2, and z=0]; and the sintering temperature was set to 1,080° C.

Example 1-5

A piezoelectric composition and a piezoelectric element were produced in the same way as in Example 1-1 except that: the starting materials used were 30 g in total of $Bi_2O_3$, $KHCO_3$, $TiO_2$, and MgO weighed such that the composition of the piezoelectric composition satisfied compositional formula $0.7(Bi_{0.5}K_{0.5})TiO_3$-$0.3Bi(Mg_{0.5}Ti_{0.5})O_3$ [x=0.7, y=0.3, and z=0]; and the sintering temperature was set to 1,070° C.

Example 1-6

A piezoelectric composition and a piezoelectric element were produced in the same way as in Example 1-1 except that: the starting materials used were 30 g in total of $Bi_2O_3$, $KHCO_3$, $TiO_2$, and MgO weighed such that the composition of the piezoelectric composition satisfied compositional formula $0.98(Bi_{0.5}K_{0.5})TiO_3$-$0.02Bi(Mg_{0.5}Ti_{0.5})O_3$ [x=0.98, y=0.02, and z=0]; and the sintering temperature was set to 1,063° C.

Comparative Example 1-1

A piezoelectric composition and a piezoelectric element were produced in the same way as in Example 1-1 except that: the starting materials used were 30 g in total of $Bi_2O_3$, $KHCO_3$, and $TiO_2$ weighed such that the composition of the piezoelectric composition satisfied compositional formula $(Bi_{0.5}K_{0.5})TiO_3$ [x=1, y=0, and z=0]; and the sintering temperature was set to 1,060±5° C.

Comparative Example 1-2

A piezoelectric composition and a piezoelectric element were produced in the same way as in Example 1-1 except that: the starting materials used were 30 g in total of $Bi_2O_3$, $KHCO_3$, $TiO_2$, and MgO weighed such that the composition of the piezoelectric composition satisfied compositional formula $0.6(Bi_{0.5}K_{0.5})TiO_3$-$0.4Bi(Mg_{0.5}Ti_{0.5})O_3$ [x=0.6, y=0.4, and z=0]; and the sintering temperature was set to 1,080° C.

Next, the following measurement was performed using the piezoelectric compositions and the piezoelectric elements of Examples 1-1 to 1-6 and Comparative Examples 1-1 and 1-2.

<Crystal Structure Analysis of Piezoelectric Composition>

The crystal structure of each obtained piezoelectric composition was analyzed by powder X-ray diffraction.

<Measurement of Piezoelectric Constant d33* of Piezoelectric Element>

The electric field-strain curve of each obtained piezoelectric element was prepared by use of a ferroelectric property evaluation system "FCE-3" manufactured by TOYO Corp. or a self-made evaluation system using a contact-type displacement gauge. The piezoelectric constant d33* was measured from this electric field-strain curve. This measurement was performed after calibration with the value of PZT having a known piezoelectric constant d33*.

Figure 7:
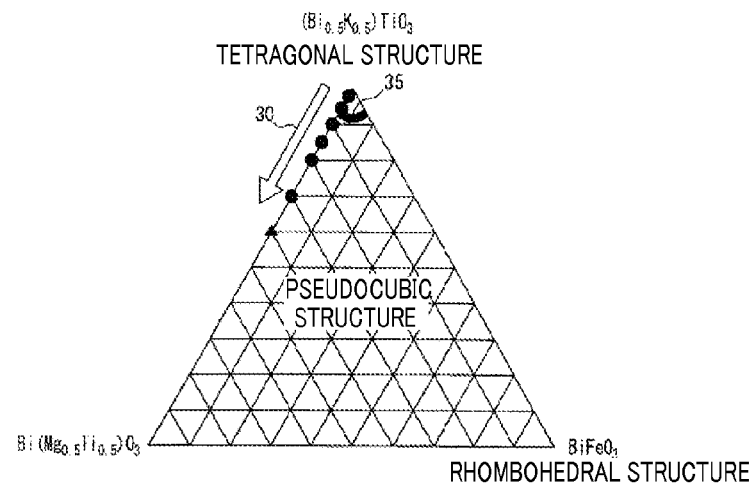
FIG. 7 illustrates triangle coordinates that indicate compositions of piezoelectric compositions of Examples 1-1 to 1-6 and Comparative Examples 1-1 and 1-2.
Figure 8:
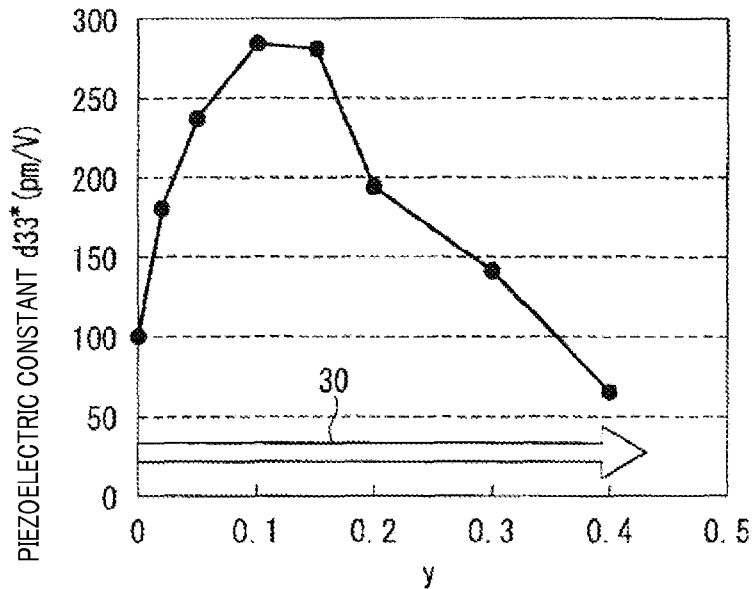
FIG. 8 illustrates the relationship between the ratio of BMT in a piezoelectric composition and a piezoelectric constant.

These results are shown in Table 1 and FIGS. 7 and 8. Table 1 also shows triangle coordinates using x, y, and z in the compositional formula of each piezoelectric composition.

TABLE 1

| | Triangle coordinates (x, y, z) | d33* (pm/V) | Crystal structure |
|---|---|---|---|
| Example 1-1 | (0.95, 0.05, 0) | 237 | Coexistence of tetragonal and pseudocubic structures |
| Example 1-2 | (0.9, 0.1, 0) | 285 | Pseudocubic structure |
| Example 1-3 | (0.85, 0.15, 0) | 278 | Pseudocubic structure |
| Example 1-4 | (0.8, 0.2, 0) | 191 | Pseudocubic structure |
| Example 1-5 | (0.7, 0.3, 0) | 145 | Pseudocubic structure |
| Example 1-6 | (0.98, 0.02, 0) | 180 | Tetragonal structure |
| Comparative Example 1-1 | (1, 0, 0) | 100 | Tetragonal structure |
| Comparative Example 1-2 | (0.6, 0.4, 0) | 64 | Coexistence of pseudocubic structure and heterogeneous phase |

The piezoelectric constants of these piezoelectric elements were measured along arrow 30 shown in FIGS. 7 and 8. As is evident from Table 1, the piezoelectric elements of Examples 1-1 to 1-6 can achieve larger piezoelectric constants than those of the piezoelectric elements of Comparative Examples 1-1 and 1-2. As is evident from Table 1 and FIG. 8, the piezoelectric elements of Examples 1-1, 1-2, and 1-3 in which y in the triangle coordinates of their piezoelectric compositions falls within the range of $0.05 \leq y \leq 0.15$ have a particularly large piezoelectric constant d33*. This is presumably because, in FIG. 7, the compositions of the piezoelectric compositions of Examples 1-1, 1-2, and 1-3 include tetragonal-pseudocubic phase boundary 35 or have composition located in proximity to phase boundary 35.

Example 1-7

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.85(Bi_{0.5}K_{0.5})TiO_3$-$0.1Bi(Mg_{0.5}Ti_{0.5})O_3$-$0.05BiFeO_3$ [x=0.85, y=0.1, and z=0.05]; and the sintering temperature was set to 1,070° C.

Example 1-8

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.8(Bi_{0.5}K_{0.5})TiO_3$-$0.1Bi(Mg_{0.5}Ti_{0.5})O_3$-$0.1BiFeO_3$ [x=0.8, y=0.1, and z=0.1]; and the sintering temperature was set to 1,055° C.

Example 1-9

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.7(Bi_{0.5}K_{0.5})TiO_3$-$0.1Bi(Mg_{0.5}Ti_{0.5})O_3$-$0.2BiFeO_3$ [x=0.7, y=0.1, and z=0.2]; and the sintering temperature was set to 1,030° C.

Example 1-10

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.6(Bi_{0.5}K_{0.5})TiO_3$-$0.1Bi(Mg_{0.5}Ti_{0.5})O_3$-$0.3BiFeO_3$ [x=0.6, y=0.1, and z=0.3]; and the sintering temperature was set to 1,000° C.

Example 1-11

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.5(Bi_{0.5}K_{0.5})TiO_3$-$0.1Bi(Mg_{0.5}Ti_{0.5})O_3$-$0.4BiFeO_3$ [x=0.5, y=0.1, and z=0.4]; and the sintering temperature was set to 1,000° C.

Example 1-12

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.45(Bi_{0.5}K_{0.5})TiO_3$-$0.1Bi(Mg_{0.5}Ti_{0.5})O_3$-$0.45BiFeO_3$ [x=0.45, y=0.1, and z=0.45]; and the sintering temperature was set to 1,000° C.

Example 1-13

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.4(Bi_{0.5}K_{0.5})TiO_3$-$0.1Bi(Mg_{0.5}Ti_{0.5})O_3$-$0.5BiFeO_3$ [x=0.4, y=0.1, and z=0.5]; and the sintering temperature was set to 1,000° C.

Example 1-14

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.3(Bi_{0.5}K_{0.5})TiO_3$-$0.1Bi(Mg_{0.5}Ti_{0.5})O_3$-$0.6BiFeO_3$ [x=0.3, y=0.1, and z=0.6]; and the sintering temperature was set to 1,000° C.

Example 1-15

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.2(Bi_{0.5}K_{0.5})TiO_3$-$0.1Bi(Mg_{0.5}Ti_{0.5})O_3$-$0.7BiFeO_3$ [x=0.2, y=0.1, and z=0.7]; and the sintering temperature was set to 950° C.

Example 1-16

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.1(Bi_{0.5}K_{0.5})TiO_3$-$0.1Bi(Mg_{0.5}Ti_{0.5})O_3$-$0.8BiFeO_3$ [x=0.1, y=0.1, and z=0.8]; and the sintering temperature was set to 950° C.

Comparative Example 1-3

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.05(Bi_{0.5}K_{0.5})TiO_3$-$0.1Bi(Mg_{0.5}Ti_{0.5})O_3$-$0.85BiFeO_3$ [x=0.05, y=0.1, and z=0.85]; and the sintering temperature was set to 900° C.

Comparative Example 1-4

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.2(Bi_{0.5}K_{0.5})TiO_3$-$0.4Bi(Mg_{0.5}Ti_{0.5})O_3$-

0.4BiFeO$_3$ [x=0.2, y=0.4, and z=0.4]; and the sintering temperature was set to 1,000° C.

(Comparative Example 1-5)

A piezoelectric composition and a piezoelectric element were produced in the same way as in Example 1-1 except that: the starting materials used were 30 g in total of Bi$_2$O$_3$, KHCO$_3$, TiO$_2$, MgO, and Fe$_2$O$_3$ weighed such that the composition of the piezoelectric composition satisfied compositional formula 0.1(Bi$_{0.5}$K$_{0.5}$)TiO$_3$-0.4Bi(Mg$_{0.5}$Ti$_{0.5}$)O$_3$-0.5BiFeO$_3$ [x=0.1, y=0.4, and z=0.5]; and the sintering temperature was set to 1,000° C.

Next, the piezoelectric compositions and the piezoelectric elements of Examples 1-7 to 1-16 and Comparative Examples 1-3 to 1-5 were used to perform the crystal structure analysis of the piezoelectric compositions and the measurement of piezoelectric constants d33* of the piezoelectric elements in the same way as in Example 1-1. The results are shown in Table 2 and FIGS. 9 and 10 ("Without annealing step"). Table 2 also shows triangle coordinates using x, y, and z in the compositional formula of each piezoelectric composition.

TABLE 2

| | Triangle coordinates (x, y, z) | d33* (pm/V) | Crystal structure |
|---|---|---|---|
| Example 1-7 | (0.85, 0.1, 0.05) | 225 | Pseudocubic structure |
| Example 1-8 | (0.8, 0.1, 0.1) | 230 | Pseudocubic structure |
| Example 1-9 | (0.7, 0.1, 0.2) | 220 | Pseudocubic structure |
| Example 1-10 | (0.6, 0.1, 0.3) | 175 | Pseudocubic structure |
| Example 1-11 | (0.5, 0.1, 0.4) | 160 | Pseudocubic structure |
| Example 1-12 | (0.45, 0.1, 0.45) | 131 | Coexistence of pseudocubic and rhombohedral structures |
| Example 1-13 | (0.4, 0.1, 0.5) | 98 | Rhombohedral structure |
| Example 1-14 | (0.3, 0.1, 0.6) | 60 | Rhombohedral structure |
| Example 1-15 | (0.2, 0.1, 0.7) | 58 | Rhombohedral structure |
| Example 1-16 | (0.1, 0.1, 0.8) | 30 | Rhombohedral structure |
| Comparative Example 1-3 | (0.05, 0.1, 0.85) | 21 | Rhombohedral structure |
| Comparative Example 1-4 | (0.2, 0.4, 0.4) | 15 | Coexistence of pseudocubic structure and heterogeneous phase |
| Comparative Example 1-5 | (0.1, 0.4, 0.5) | 15 | Coexistence of pseudocubic structure and heterogeneous phase |

Figure 9:
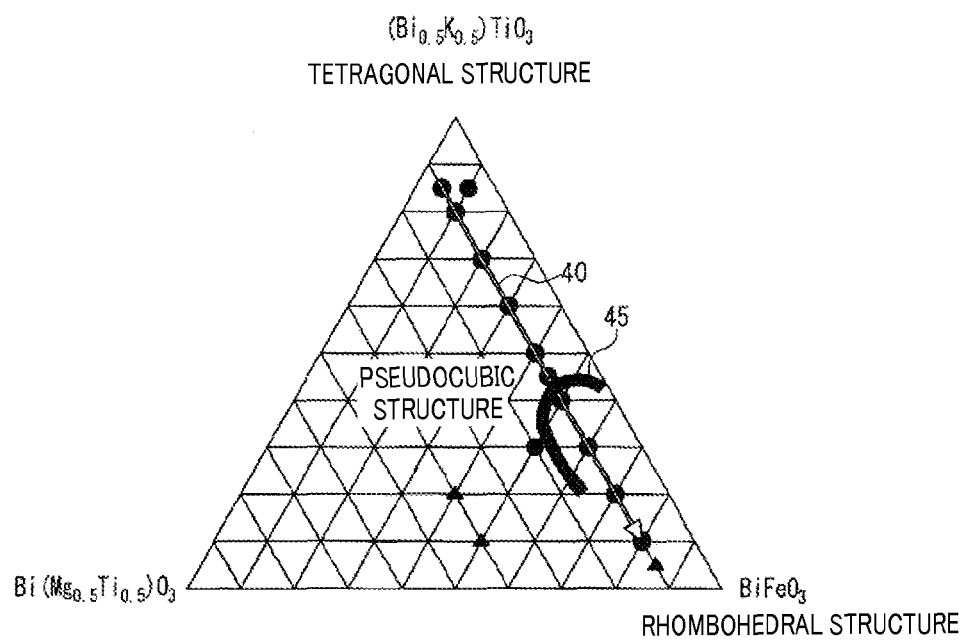
FIG. 9 illustrates triangle coordinates that indicate compositions of piezoelectric compositions of Examples 1-7 to 1-26 and Comparative Examples 1-3 to 1-6.
Figure 10:
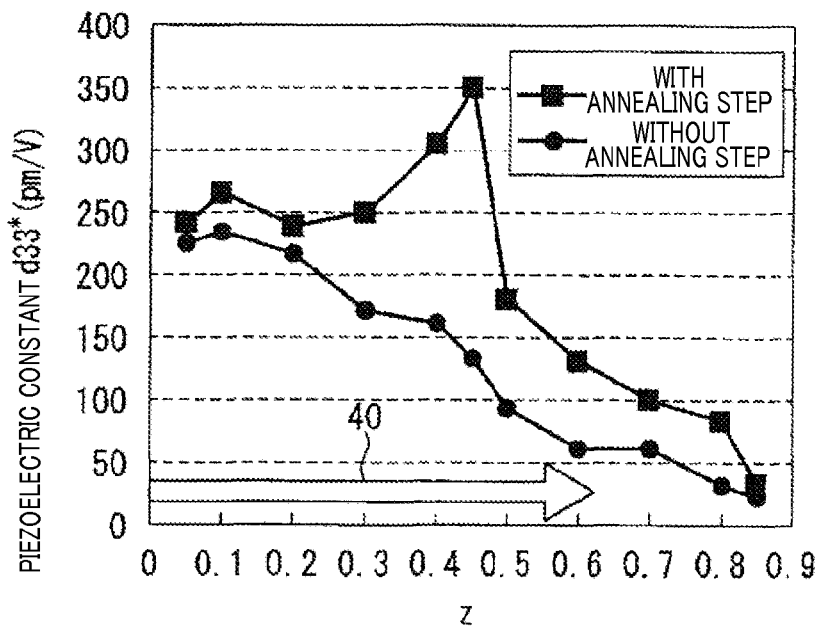
FIG. 10 illustrates the relationship between the ratio of BFO in a piezoelectric composition and a piezoelectric constant.

The piezoelectric constants of these piezoelectric elements were measured along arrow 40 shown in FIGS. 9 and 10. As is evident from Table 2, the piezoelectric elements of Examples 1-7 to 1-16 can achieve larger piezoelectric constants than those of the piezoelectric elements of Comparative Examples 1-3 to 1-5.

Next, Examples based on the second method for producing the piezoelectric composition of the first aspect will be described.

Example 1-17

Starting Material Preparation Step

A starting material compact was obtained in the same way as in Example 1-1 except that the starting materials used were 30 g in total of Bi$_2$O$_3$, KHCO$_3$, TiO$_2$, MgO, and Fe$_2$O$_3$ weighed such that the composition of the resulting piezoelectric composition satisfied compositional formula 0.85(Bi$_{0.5}$K$_{0.5}$)TiO$_3$-0.1Bi(Mg$_{0.5}$Ti$_{0.5}$)O$_3$-0.05BiFeO$_3$ [x=0.85, y=0.1, and z=0.05].

<Temperature Elevation Step>

Next, the temperature of the obtained starting material compact was elevated to 1,070° C. at a rate of temperature rise of 300° C./hr.

<First Heat Treatment Step>

Next, the starting material compact was sintered at 1,070° C. for 2 hours.

<Temperature Lowering Step>

Next, the temperature of the compact thus sintered was lowered to 800° C. at a rate of 300° C./hr.

<Second Heat Treatment Step (Annealing Step)>

Subsequently, the temperature-lowered compact was annealed at 800° C. for 20 hours.

<Cooling Step>

Finally, the compact thus annealed was cooled to room temperature at a rate of cooling of 40 to 100° C./second to obtain a piezoelectric composition.

Next, the obtained piezoelectric composition was processed into a thickness of approximately 0.4 mm by polishing. Then, gold electrodes were formed on both sides of the piezoelectric composition by sputtering to obtain a piezoelectric element.

Example 1-18

A piezoelectric composition and a piezoelectric element were produced in the same way as in Example 1-17 except that: the starting materials used were 30 g in total of Bi$_2$O$_3$, KHCO$_3$, TiO$_2$, MgO, and Fe$_2$O$_3$ weighed such that the composition of the piezoelectric composition satisfied compositional formula 0.8(Bi$_{0.5}$K$_{0.5}$)TiO$_3$-0.1Bi(Mg$_{0.5}$Ti$_{0.5}$)O$_3$-0.1BiFeO$_3$ [x=0.8, y=0.1, and z=0.1]; and the sintering temperature was set to 1,055° C.

Example 1-19

A piezoelectric composition and a piezoelectric element were produced in the same way as in Example 1-17 except that: the starting materials used were 30 g in total of Bi$_2$O$_3$, KHCO$_3$, TiO$_2$, MgO, and Fe$_2$O$_3$ weighed such that the composition of the piezoelectric composition satisfied compositional formula 0.7(Bi$_{0.5}$K$_{0.5}$)TiO$_3$-0.1Bi(Mg$_{0.5}$Ti$_{0.5}$)O$_3$-0.2BiFeO$_3$ [x=0.7, y=0.1, and z=0.2]; and the sintering temperature was set to 1,030° C.

Example 1-20

A piezoelectric composition and a piezoelectric element were produced in the same way as in Example 1-17 except that: the starting materials used were 30 g in total of Bi$_2$O$_3$, KHCO$_3$, TiO$_2$, MgO, and Fe$_2$O$_3$ weighed such that the composition of the piezoelectric composition satisfied compositional formula 0.6(Bi$_{0.5}$K$_{0.5}$)TiO$_3$-0.1Bi(Mg$_{0.5}$Ti$_{0.5}$)O$_3$-0.3BiFeO$_3$ [x=0.6, y=0.1, and z=0.3]; and the sintering temperature was set to 1,000° C.

Example 1-21

A piezoelectric composition and a piezoelectric element were produced in the same way as in Example 1-17 except that: the starting materials used were 30 g in total of Bi$_2$O$_3$, KHCO$_3$, TiO$_2$, MgO, and Fe$_2$O$_3$ weighed such that the composition of the piezoelectric composition satisfied compositional formula 0.5(Bi$_{0.5}$K$_{0.5}$)TiO$_3$-0.1Bi(Mg$_{0.5}$Ti$_{0.5}$)O$_3$-0.4BiFeO$_3$ [x=0.5, y=0.1, and z=0.4]; and the sintering temperature was set to 1,000° C.

Example 1-22

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.45(Bi_{0.5}K_{0.5})TiO_3$-$0.1Bi(Mg_{0.5}Ti_{0.5})O_3$-$0.45BiFeO_3$ [x=0.45, y=0.1, and z=0.45]; and the sintering temperature was set to 1,000° C.

Example 1-23

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.4(Bi_{0.5}K_{0.5})TiO_3$-$0.1Bi(Mg_{0.5}Ti_{0.5})O_3$-$0.5BiFeO_3$ [x=0.4, y=0.1, and z=0.5]; and the sintering temperature was set to 1,000° C.

Example 1-24

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.3(Bi_{0.5}K_{0.5})TiO_3$-$0.1Bi(Mg_{0.5}Ti_{0.5})O_3$-$0.6BiFeO_3$ [x=0.3, y=0.1, and z=0.6]; and the sintering temperature was set to 1,000° C.

Example 1-25

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.2(Bi_{0.5}K_{0.5})TiO_3$-$0.1Bi(Mg_{0.5}Ti_{0.5})O_3$-$0.7BiFeO_3$ [x=0.2, y=0.1, and z=0.7]; and the sintering temperature was set to 1,000° C.

Example 1-26

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.1(Bi_{0.5}K_{0.5})TiO_3$-$0.1Bi(Mg_{0.5}Ti_{0.5})O_3$-$0.8BiFeO_3$ [x=0.1, y=0.1, and z=0.8]; and the sintering temperature was set to 950° C.

Comparative Example 1-6

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.05(Bi_{0.5}K_{0.5})TiO_3$-$0.1Bi(Mg_{0.5}Ti_{0.5})O_3$-$0.85BiFeO_3$ [x=0.05, y=0.1, and z=0.85]; and the sintering temperature was set to 900° C.

Next, the piezoelectric compositions and the piezoelectric elements of Examples 1-17 to 1-26 and Comparative Example 1-6 were used to perform the crystal structure analysis of the piezoelectric compositions and the measurement of piezoelectric constants d33* of the piezoelectric elements in the same way as in Example 1-1. The results are shown in Table 3 and FIGS. 9 and 10 ("With annealing step"). Table 3 also shows triangle coordinates using x, y, and z in the compositional formula of each piezoelectric composition.

TABLE 3

| | Triangle coordinates (x, y, z) | d33* (pm/V) | Crystal structure |
|---|---|---|---|
| Example 1-17 | (0.85, 0.1, 0.05) | 240 | Coexistence of tetragonal and pseudocubic structures |
| Example 1-18 | (0.8, 0.1, 0.1) | 262 | Pseudocubic structure |
| Example 1-19 | (0.7, 0.1, 0.2) | 236 | Pseudocubic structure |
| Example 1-20 | (0.6, 0.1, 0.3) | 250 | Pseudocubic structure |
| Example 1-21 | (0.5, 0.1, 0.4) | 302 | Pseudocubic structure |
| Example 1-22 | (0.45, 0.1, 0.45) | 351 | Coexistence of pseudocubic and rhombohedral structures |
| Example 1-23 | (0.4, 0.1, 0.5) | 170 | Coexistence of pseudocubic and rhombohedral structures |
| Example 1-24 | (0.3, 0.1, 0.6) | 130 | Rhombohedral structure |
| Example 1-25 | (0.2, 0.1, 0.7) | 98 | Rhombohedral structure |
| Example 1-26 | (0.1, 0.1, 0.8) | 83 | Rhombohedral structure |
| Comparative Example 1-6 | (0.05, 0.1, 0.85) | 30 | Rhombohedral structure |

The piezoelectric constants of these piezoelectric elements were measured along arrow 40 shown in FIGS. 9 and 10. As is evident from Table 3, the piezoelectric elements of Examples 1-17 to 1-26 can achieve larger piezoelectric constants than those of the piezoelectric element of Comparative Example 1-6. As is evident from Table 3 and FIG. 10, the piezoelectric elements of Examples 1-21 and 1-22 in which z in the triangle coordinates of their piezoelectric compositions falls within the range of $0.4 \leq z \leq 0.45$ have a particularly large piezoelectric constant. This is presumably because, in FIG. 9, the compositions of the piezoelectric compositions of Examples 1-21 and 1-22 include pseudocubic-rhombohedral phase boundary 45 or have composition located in proximity to phase boundary 45.

When the sintering time of the first heat treatment step in Example 1-22 was further increased to 20 to 300 hours, greater piezoelectric properties (d33*: 378 to 410 pm/V) were successfully obtained.

Next, the influence of an additive on the piezoelectric composition of the first aspect will be discussed.

Example 1-27

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.45(Bi_{0.5}K_{0.5})TiO_3$-$0.1Bi(Mg_{0.5}Ti_{0.5})O_3$-$0.45BiFeO_3$ [x=0.45, y=0.1, and z=0.45]; 0.2 wt % (0.06 g) of $MnCO_3$ was further added to this 30 g of the starting materials; the sintering temperature was set to 1,000° C.; and the sintering time was set to 20 hours.

In addition, piezoelectric compositions and piezoelectric elements were produced in the same way as above except that the amount of $MnCO_3$ added was changed to 0.05 to 0.5 wt %.

Figure 11:
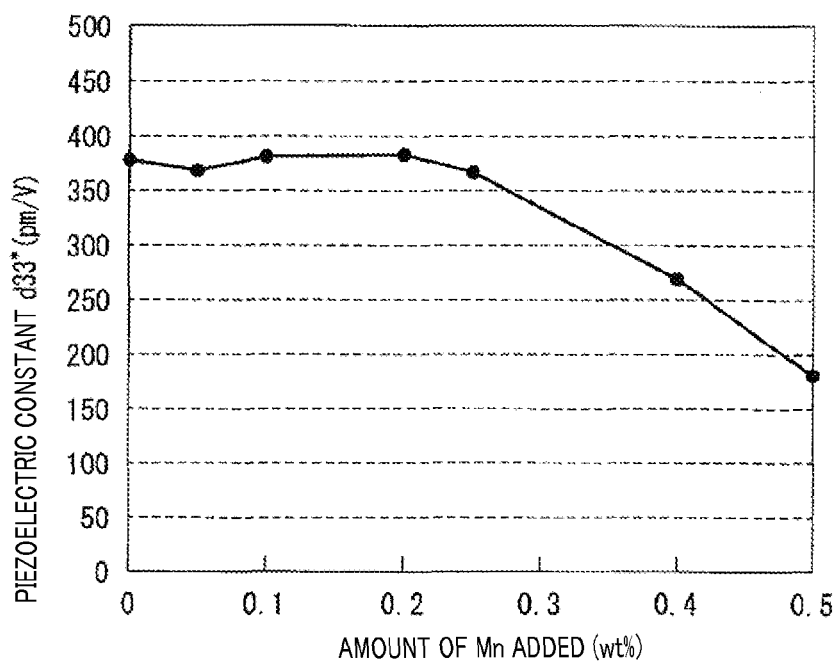
FIG. 11 illustrates the relationship between the amount of Mn added in a piezoelectric composition and a piezoelectric constant.
Figure 12:
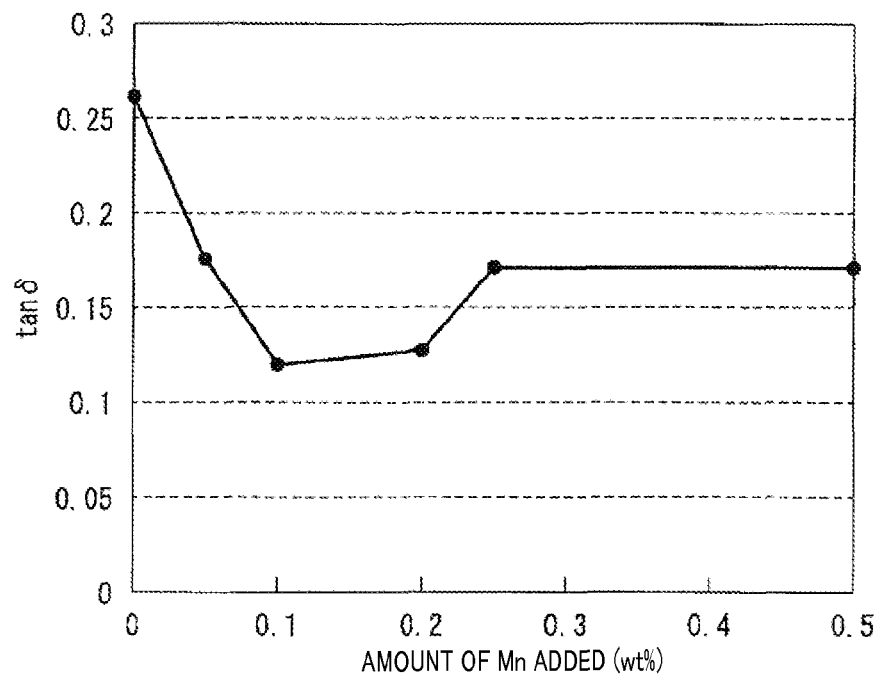
FIG. 12 illustrates the relationship between the amount of Mn added in a piezoelectric composition and a dielectric loss.

Next, the produced piezoelectric elements were used to measure the piezoelectric constants d33* of the piezoelectric elements in the same way as in Example 1-1. The results are shown in FIG. 11. Also, the dielectric losses (tan δ) of the produced piezoelectric elements were measured at a frequency of 100 Hz and a temperature of 150° C. using an LCR meter (model 6440B) manufactured by Wayne Kerr Electronics. The results are shown in FIG. 12.

As is evident from FIG. 11, the value of the piezoelectric constant d33* rarely drops until the amount of $MnCO_3$ added reaches 0.3 wt %. As is evident from FIG. 12, the dielectric loss (tan δ) drops rapidly by the addition of $MnCO_3$. This means that leak current is reduced during application of high voltage. These results demonstrated that the addition of $MnCO_3$ is very advantageous for polarization treatment, because this addition reduces leak current during application of high voltage and, even in a small amount, rarely causes a drop in piezoelectric constant d33*. The Mn additive used in this Example was $MnCO_3$. Likewise, use of MnO, $Mn_2O_3$, $MnO_2$, $Mn_3O_4$, or the like can also reduce dielectric loss (tan δ) at a low frequency and 150° C.

Example 1-28

A piezoelectric composition and a piezoelectric element were produced in the same way as in Example 1-1 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.427(Bi_{0.5}K_{0.5})TiO_3$-$0.05Bi(Mg_{0.5}Ti_{0.5})O_3$-$0.523BiFeO_3$ [x=0.427, y=0.05, and z=0.523]; the sintering temperature was set to 1,000° C.; and the sintering time was set to 20 hours.

Example 1-29

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.427(Bi_{0.5}K_{0.5})TiO_3$-$0.05Bi(Mg_{0.5}Ti_{0.5})O_3$-$0.523BiFeO_3$ [x=0.427, y=0.05, and z=0.523]; the sintering temperature was set to 1,000° C.; and the sintering time was set to 20 hours.

Next, the piezoelectric compositions and the piezoelectric elements of Examples 1-28 and 1-29 were used to perform the crystal structure analysis of the piezoelectric compositions and the measurement of piezoelectric constants d33* of the piezoelectric elements in the same way as in Example 1-1. The results are shown in Table 4. Table 4 also shows triangle coordinates using x, y, and z in the compositional formula of each piezoelectric composition.

TABLE 4

| | Triangle coordinates (x, y, z) | d33* (pm/V) | Crystal structure |
|---|---|---|---|
| Example 1-28 | (0.427, 0.05, 0.523) | 290 | Coexistence of pseudo-cubic and rhombohedral structures |
| Example 1-29 | (0.427, 0.05, 0.523) | 288 | Coexistence of pseudo-cubic and rhombohedral structures |

Figure 13:
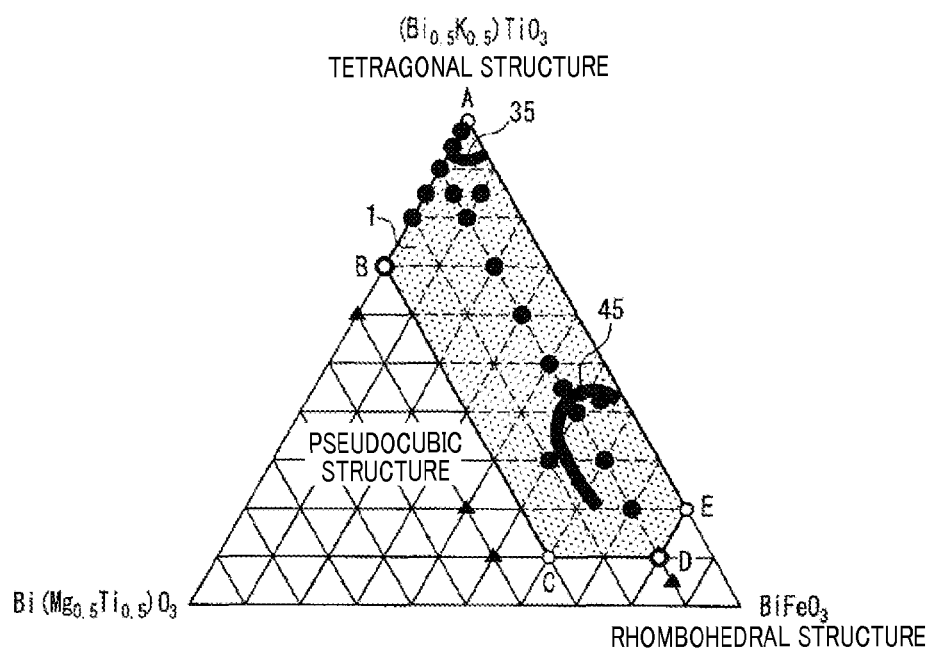
FIG. 13 illustrates triangle coordinates that define composition regions of piezoelectric compositions based on Examples 1-1 to 1-31 and Comparative Examples 1-1 to 1-6.
Figure 14:
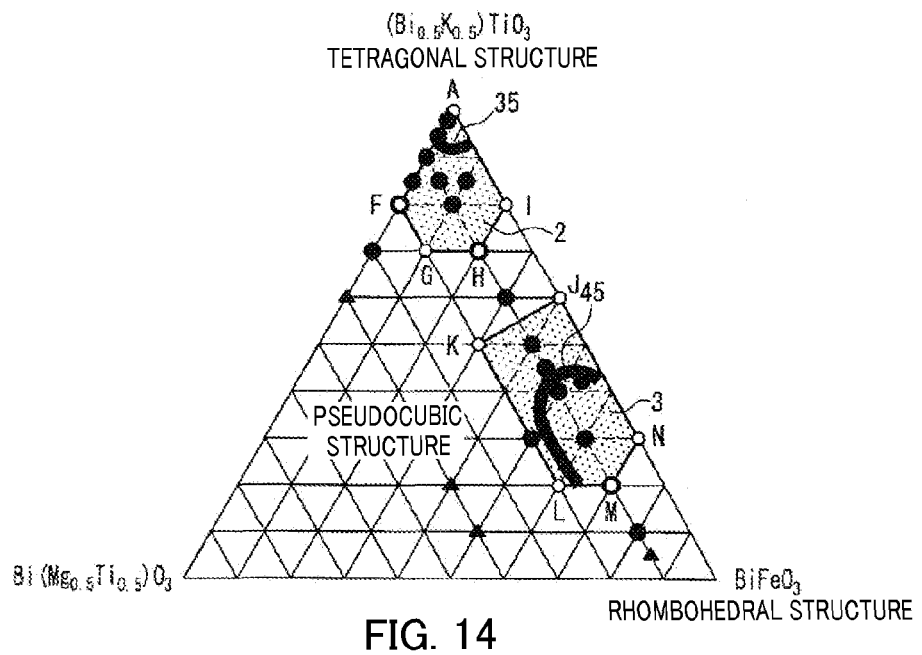
FIG. 14 illustrates triangle coordinates that define more preferred composition regions of piezoelectric compositions based on Examples 1-1 to 1-31 and Comparative Examples 1-1 to 1-6.

As is evident from Table 4, the piezoelectric elements of Examples 1-28 and 1-29 in which the sintering time was merely changed to a long time in comparison with Comparative Examples 1-3 to 1-5 and 1-6 can achieve large piezoelectric constants even without the second heat treatment step. This is presumably because, as illustrated in FIGS. 13 and 14 mentioned later, the compositions of the piezoelectric compositions of Examples 1-28 and 1-29 include pseudocubic-rhombohedral phase boundary 45.

Example 1-30

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.427(Bi_{0.5}K_{0.5})TiO_3$-$0.05Bi(Mg_{0.5}Ti_{0.5})O_3$-$0.523BiFeO_3$ [x=0.427, y=0.05, and z=0.523]; 0.1 wt % (0.03 g) of $Nb_2O_5$ was further added to this 30 g of the starting materials; the sintering temperature was set to 1,000° C.; and the sintering time was set to 20 hours.

Example 1-31

A piezoelectric composition and a piezoelectric element were produced in the same way as in Example 1-17 except that: the starting materials used were 30 g in total of $Bi_2O_3$, $KHCO_3$, $TiO_2$, MgO, and $Fe_2O_3$ weighed such that the composition of the piezoelectric composition satisfied compositional formula $0.427(Bi_{0.5}K_{0.5})TiO_3$-$0.05Bi(Mg_{0.5}Ti_{0.5})O_3$-$0.523BiFeO_3$ [x=0.427, y=0.05, and z=0.523]; 0.1 wt % (0.03 g) of WO3 was further added to this 30 g of the starting materials; the sintering temperature was set to 1,000° C.; and the sintering time was set to 20 hours.

Next, the piezoelectric elements of Examples 1-30 and 1-31 were used to measure their piezoelectric constants d33* in the same way as in Example 1-1. The results are shown in Table 5. Table 5 also shows triangle coordinates using x, y, and z in the compositional formula of each piezoelectric composition.

TABLE 5

| | Triangle coordinates (x, y, z) | d33* (pm/V) | Additive |
|---|---|---|---|
| Example 1-30 | (0.427, 0.05, 0.523) | 320 | $Nb_2O_5$ |
| Example 1-31 | (0.427, 0.05, 0.523) | 297 | $WO_3$ |

As is evident from Table 5, the piezoelectric elements of Examples 1-30 and 1-31 in which the piezoelectric composition of Example 1-29 was merely supplemented with an additive can achieve large piezoelectric constants. The additives used in Examples 1-27 to 1-31 were $MnCO_3$, $Nb_2O_5$, and $WO_3$ each separately added. The simultaneous addition of these additives can achieve a piezoelectric composition and a piezoelectric element having high insulation properties and high piezoelectricity.

FIGS. 13 and 14 summarize the composition regions of Examples 1-1 to 1-31 and Comparative Examples 1-1 to 1-6. In FIG. 13, the piezoelectric compositions in composition region 1 that is enclosed by pentagon ABCDE but exclusive of segment AE have a large piezoelectric constant d33*. In FIG. 14, the piezoelectric compositions in composition region 2 that is enclosed by pentagon AFGHI but exclusive of segment AI and composition region 3 that is enclosed by pentagon JKLMN but exclusive of segment JN have a particularly large piezoelectric constant d33*.

As described above, the piezoelectric composition of the first aspect is a lead-free piezoelectric composition that has a large piezoelectric constant and can be produced with high reproducibility by a convenient method. Thus, the piezoelectric composition of the first aspect can be expected to be applied as an environment-responsive piezoelectric composition containing no lead to ultrasonic probes, transducers, and sensors.

Second Aspect

Hereinafter, the second aspect will be described.

Embodiment 2-1

First, the lead-free piezoelectric element of the second aspect will be described.

The lead-free piezoelectric element of the second aspect includes a piezoelectric composition and an electrode that applies voltage to the piezoelectric composition. The piezoelectric composition has a perovskite structure represented by general compositional formula $ABO_3$ and contains $BiFeO_3$ and a Bi complex oxide. The $BiFeO_3$ has a content of 3 to 80 mol % with respect to the whole piezoelectric composition. The Bi complex oxide contains Bi at site A in the general compositional formula and a plurality of elements differing in valence at site B therein. The lead-free piezoelectric element has a relative permittivity er of 400 or larger and a dielectric loss tan δ of 0.2 or smaller at 25° C. (room temperature), and has a piezoelectric constant d33* of 250 pm/V or higher determined from an electric field-strain curve.

Use of this piezoelectric composition can provide a lead-free piezoelectric element having a large spontaneous polarization or remnant polarization, small leak current, and high piezoelectric properties.

The piezoelectric composition has a perovskite structure which is represented by general compositional formula $ABO_3$. The standard molar ratio of the site-A element, the site-B element, and oxygen is 1:1:3. The molar ratio of these moieties may fall outside the standard molar ratio within a range that can form the perovskite structure. In the second aspect, site B is composed of a plurality of elements differing in valence. Examples of the site-B elements include Mg, Zn, Ti, Zr, Fe, Mn, Co, Ni, Nb, Ta, and W.

Preferably, the composition of the piezoelectric composition includes a phase boundary between at least 2 types of crystal structures or has composition located in proximity to the phase boundary. This can further improve the piezoelectric properties of the lead-free piezoelectric element. In this context, the phase boundary refers to a composition region in which at least 2 types of crystal structures coexist with each other. The composition located in proximity to the phase boundary according to the second aspect is defined as a composition region that includes at least the phase boundary within 15 mol % from the predetermined composition and further involves the maximum value of piezoelectric constant d33* determined from an electric field-strain curve. Specifically, the phase boundary may be a composition region in which a rhombohedral structure coexists with any one crystal structure selected from the group consisting of pseudocubic, tetragonal, orthorhombic, and monoclinic structures, or may be a composition region in which tetragonal and pseudocubic structures coexist with each other.

The piezoelectric constant d33* is preferably 330 pm/V or higher. The $BiFeO_3$ content is preferably 30 to 80 mol % with respect to the whole piezoelectric composition. This can further improve the piezoelectric properties of the lead-free piezoelectric element.

The piezoelectric composition is preferably made of a relaxor material. The relaxor according to the second aspect refers to a complex oxide that has a perovskite structure represented by general compositional formula $ABO_3$ with site A or site B composed of a plurality of elements and has a broad peak of permittivity in response to change in temperature. The lead-free piezoelectric element having a broad peak of permittivity in terms of relaxor properties exhibits high permittivity even at a temperature different from the peak temperature. Such a piezoelectric element that exhibits relaxor properties is useful for devices required to have high permittivity, such as ultrasonic probes.

The piezoelectric composition is preferably made of a ceramic having a particle size of 0.5 μm or larger and 200 μm or smaller, more preferably made of a ceramic having a particle size of 1 μm or larger and 100 μm or smaller. The particle size set to 0.5 μm or larger can increase a relative permittivity em at maximum temperature Tm. This is advantageous for increasing a permittivity at room temperature or a remnant polarization. The upper limit of the particle size is based on the workability of the piezoelectric composition. The particle size set to 200 μm or smaller can prevent a fracture in the ceramic.

The piezoelectric composition may be composed of a single crystal. The particle size of the single crystal does not matter. The single crystal needs to have strength that resists processing as a piezoelectric material.

Preferably, the piezoelectric composition further includes $(Bi_{0.5}K_{0.5})TiO_3$ and $Bi(Mg_{0.5}Ti_{0.5})O_3$. More specifically, the piezoelectric composition is represented by compositional formula $x(Bi_{0.5}K_{0.5})TiO_3$-$yBi(Mg_{0.5}Ti_{0.5})O_3$-$zBiFeO_3$. In the compositional formula, $x+y+z=1$ is preferred. The BKT-BMT-BFO complex composition can yield a piezoelectric composition having a larger piezoelectric constant than that of each of BKT alone, BMT alone, and BFO alone.

For the piezoelectric composition, Mg in the compositional formula is preferably partially replaced with Zn, and Bi in the compositional formula is preferably partially replaced with at least one type selected from La, Sm, and Nd. Furthermore, Ti in the compositional formula is preferably partially replaced with Zr. The replacement of these elements can lower curie temperature (Tc) or maximum temperature (Tm) of permittivity. Tc (or Tm) thus lowered can be expected to produce a large piezoelectric constant and a large permittivity in the piezoelectric composition of the second aspect that exhibits relaxor properties.

Preferably, the piezoelectric composition further contains 2 wt % or less of at least one element selected from the group consisting of Mn, Co, Ni, V, Nb, Ta, W, Si, Ge, Ca, and Sr. Mn, Co, Ni, or V thus contained therein can enhance insulation properties and can be expected to reduce leak current. In this context, $MnCO_3$, $MnO$, $Mn_2O_3$, $Mn_3O_4$, $MnO_2$, or the like can be used as a Mn source. V, Nb, Ta, or W is preferred as a dopant advantageous for softening the piezoelectric composition. Si or Ge thus contained therein is advantageous for improving sintered density and for improving an electromechanical coupling coefficient. Ca or Sr thus contained therein can be expected to reduce the evaporation of Bi or K and consequently, can improve properties or reliability.

At least one element selected from the group consisting of Mn, Co, Ni, V, Nb, Ta, W, Si, Ge, Ca, and Sr mentioned above does not have to be dissolved in the crystal of the piezoelectric composition and may be deposited in crystal grains or grain boundary or may be segregated.

The lead-free piezoelectric element of the second aspect has a relative permittivity ∈m of preferably 7,000 or larger, more preferably 13,000 or larger, at maximum temperature Tm. In this context, the maximum temperature Tm refers to a temperature at which the relative permittivity exhibits the largest value. Also, the lead-free piezoelectric element of the second aspect has a dielectric loss tan δ of preferably 0.2 or smaller. For the lead-free piezoelectric element of the second aspect, the maximum temperature Tm is preferably 130° C. or higher and 400° C. or lower. This renders the lead-free piezoelectric element usable in a practical temperature range and can lower maximum temperature Tm or curie temperature Tc in comparison to BFO, thereby easily increasing a relative permittivity ∈r at room temperature. The relative permittivity according to the second aspect is defined as a value measured at a frequency of 1 MHz, unless otherwise specified. The lead-free piezoelectric element of the second aspect has a remnant polarization Pr of preferably 20 $\mu C/cm^2$ or larger.

Next, the lead-free piezoelectric element of the second aspect will be described with reference to the accompanying drawings.

Figure 15:
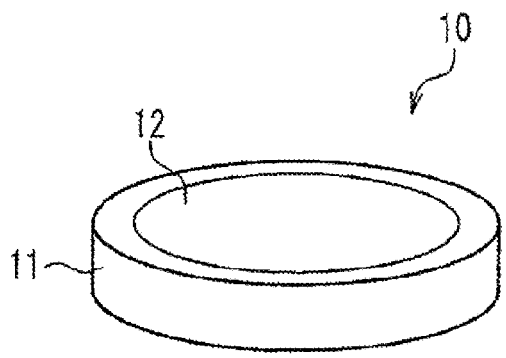
FIG. 15 is a perspective view illustrating one example of the lead-free piezoelectric element of the second aspect.
Figure 16:
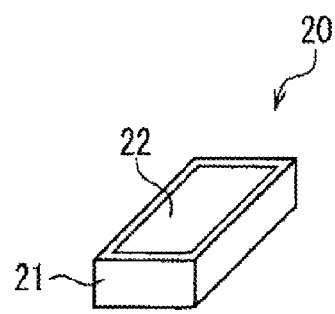
FIG. 16 is a perspective view illustrating another example of the lead-free piezoelectric element of the second aspect.

FIG. 15 is a perspective view illustrating one example of the lead-free piezoelectric element of the second aspect. In FIG. 15, piezoelectric element 10 of the second aspect includes piezoelectric composition 11 and electrode 12 that applies voltage to piezoelectric composition 11. FIG. 16 is a perspective view illustrating another example of the lead-free piezoelectric element of the second aspect. In FIG. 16, piezoelectric element 20 of the second aspect includes piezoelectric composition 21 and electrode 22 that applies voltage to piezoelectric composition 21. The piezoelectric composition described in this Embodiment is used as piezoelectric composition 11 or 21. Electrode 12 or 22 applies voltage to piezoelectric composition 11 or 21. Electrode 12 or 22 is not particularly limited by its material, production method, etc. and can be formed by, for example, the sputtering, vapor deposition, or printing of a metal such as gold, silver, platinum, palladium, nickel, copper, or an alloy of various noble metals.

The lead-free piezoelectric element is not particularly limited by its shape and may have any of shapes other than those shown in FIGS. 15 and 16. For example, a doughnut-like, cylindrical, or prismatic shape can be appropriately adopted depending on the use of the lead-free piezoelectric element.

Embodiment 2-2

Next, a method for producing the lead-free piezoelectric element of the second aspect will be described. The production method given below can conveniently produce the lead-free piezoelectric element described above in Embodiment 2-1.

A first method for producing the lead-free piezoelectric element of the second aspect includes a starting material preparation step, a temperature elevation step, a first heat treatment step, a temperature lowering step, a second heat treatment step, and a cooling step in the order presented to produce a piezoelectric composition contained in the lead-free piezoelectric element.

A second method for producing the lead-free piezoelectric element of the second aspect includes a starting material preparation step, a first temperature elevation step, a first heat treatment step, a first cooling step, a second temperature elevation step, a second heat treatment step, and a second cooling step in the order presented to produce a piezoelectric composition contained in the lead-free piezoelectric element.

The first and second methods for producing the lead-free piezoelectric element of the second aspect can provide a lead-free piezoelectric element having a large spontaneous polarization or remnant polarization, small leak current, and high piezoelectric properties. This is presumably because the conventional piezoelectric composition is produced merely by a starting material preparation step, a temperature elevation step, a heat treatment step, and a cooling step, whereas the piezoelectric composition according to the second aspect is produced by a process involving a first heat treatment step and a second heat treatment step. Hereinafter, this will be described with reference to the accompanying drawings.

Figure 17A:
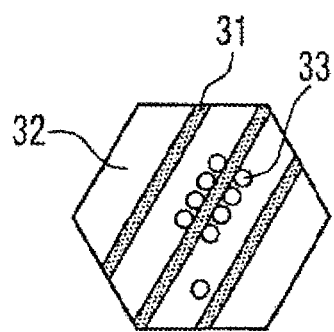
FIGS. 17A and 17B schematically illustrate the domain pinning of a lead-free piezoelectric element including a piezoelectric composition containing $BiFeO_3$, and a state where the domain pinning is avoided.
Figure 17B:
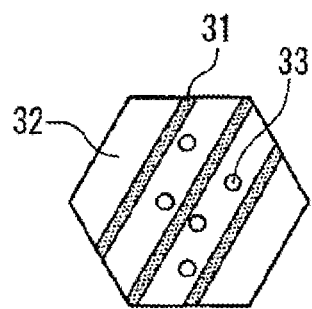

FIGS. 17A and 17B schematically illustrate the domain pinning of a lead-free piezoelectric element including a piezoelectric composition containing $BiFeO_3$ (hereinafter, also referred to as a BFO-based lead-free piezoelectric element) and a state where the domain pinning is avoided. In FIGS. 17A and 17B, defects 33 (including defect pairs) exist in the interiors of domains 32 partitioned by domain walls 31 or in contact with the domain walls.

In the BFO-based lead-free piezoelectric element, as illustrated in FIG. 17A, domains 32 or domain walls 31 are usually pinned by defects 33 such as Bi vacancy, oxygen vacancy, or $Fe^{2+}$. Furthermore, the valence of iron supposed to be $Fe^{3+}$ is changed to $Fe^{2+}$ due to, for example, oxygen vacancy generated, resulting in deteriorated insulation properties of the piezoelectric composition. The first heat treatment step and the second heat treatment step are important for preventing the pinning and the deterioration of the insulation properties of the piezoelectric composition.

In the first heat treatment step serving mainly as a sintering step, a longer sintering time can increase the particle size of the piezoelectric composition and further improve crystallinity in crystal grains. This probably increases the mobility of the domain walls. While the particle size of the piezoelectric composition is increased, impurities are ejected from the crystal grains. This step therefore helps particularly improve insulation resistance on the low frequency side and is effective for polarization treatment or reduction in dielectric loss tan δ.

The second heat treatment step serving as an annealing step can decrease the amount of defects such as oxygen vacancy or $Fe^{2+}$ and can thus reduce defect density. The subsequent cooling step can be started from an annealing temperature lower than the sintering temperature. Defects or defect pairs that cannot be removed completely may be therefore fixed before gathering at domain walls. As a result, as illustrated in FIG. 17B, various defects or defect pairs can be prevented from pinning domains and domain walls. Since the annealing temperature is lower than the sintering temperature, even cooling at a relatively fast rate produces only small temperature difference from room temperature. This can reduce thermal shock and can prevent the piezoelectric composition from being destroyed during the cooling step.

When the piezoelectric composition includes a phase boundary between 2 types of crystal structures, the absence of leak or domain wall pinning can solve the conventional problems associated with reproducibility. As a result, the piezoelectric element can exert its original piezoelectric performance with high reproducibility. This can increase a permittivity at room temperature or a remnant polarization and can achieve a lead-free piezoelectric element having a relative permittivity ∈r of 400 or larger and a dielectric loss tan δ of 0.2 or smaller at 25° C. and having a piezoelectric constant d33* of 250 pm/V or higher determined from an electric field-strain curve.

As described in Embodiment 2-1, the piezoelectric composition contains 3 to 80 mol %, more preferably 30 to 80 mol %, of BiFeO$_3$. This is because the BFO-based piezoelectric composition can easily exert its original performance of high piezoelectric properties in the absence of leak or domain wall pinning As described in Embodiment 2-1, the piezoelectric composition is preferably made of a relaxor material. This is because a peak of permittivity vs. temperature is broad and a permittivity at room temperature is easily improved. Particularly, in the case of an ultrasonic device that is driven at a relatively high frequency on the order of 1 MHz to 100 MHz, the piezoelectric element easily constitutes a 50-ohm signal processing circuit and easily attains impedance matching between a signal generator/transmission line and the piezoelectric element.

Subsequently, each method for producing the lead-free piezoelectric element of the second aspect will be further described with reference to the accompanying drawings. For the sake of convenience, the $(Bi_{0.5}K_{0.5})TiO_3$—$Bi(Mg_{0.5}Ti_{0.5})O_3$—$BiFeO_3$ system will be mainly described. However, the production method according to the second aspect is not particularly limited by this system and can be applied to other systems for use in the lead-free piezoelectric element of the second aspect.

[First Production Method]

Figure 18:
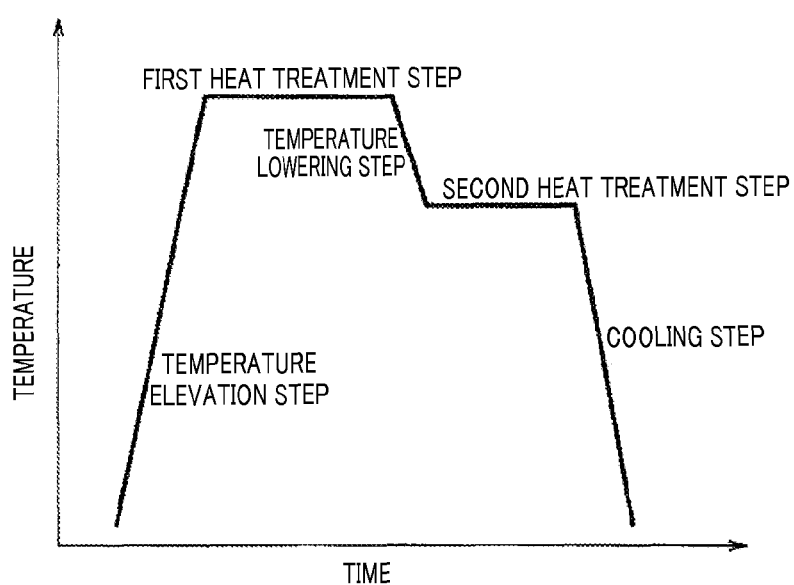
FIG. 18 schematically illustrates a first method for producing the lead-free piezoelectric element of the second aspect except for a starting material preparation step.

FIG. 18 schematically illustrates a first method for producing the lead-free piezoelectric element of the second aspect except for a starting material preparation step. The first method for producing the lead-free piezoelectric element of the second aspect includes a starting material preparation step, a temperature elevation step, a first heat treatment step, a temperature lowering step, a second heat treatment step, and a cooling step in the order presented to produce a piezoelectric composition contained in the lead-free piezoelectric element. Hereinafter, each step will be described.

<Starting Material Preparation Step>

First, oxide, carbonate, bicarbonate, various acid salts, or the like of each element constituting the piezoelectric composition is prepared as a starting material. For example, $Bi_2O_3$, $Fe_2O_3$, $TiO_2$, and MgO can be used as oxides. Also, $K_2CO_3$ or $KHCO_3$ can be used as carbonate.

As mentioned above, $K_2CO_3$ or $KHCO_3$ can be used as a potassium source for the piezoelectric composition of the second aspect. Preferably, $KHCO_3$ is used. This is because $KHCO_3$ has much smaller hygroscopicity than that of $K_2CO_3$ and can therefore reduce weighing errors as a starting material.

Next, a mixture of starting material powders is prepared using necessary amounts of weighed starting materials. The method for preparing the mixture can be any of dry and wet methods. Wet grinding using, for example, a ball mill or a jet mill can be appropriately used. In the case of performing the wet grinding using a ball mill, the starting materials are mixed with a dispersion medium, and this mixture is added to a grinding apparatus. Pure water, any of various alcoholic materials (e.g., methanol and ethanol), any of various organic liquids, or the like can be used as the dispersion medium. A grinding medium such as zirconia balls or alumina balls is further added to the grinding apparatus where mixing and grinding are then carried out until the grain size of the starting materials becomes fine and uniform. Next, the grinding medium such as zirconia balls or alumina balls is removed, and the dispersion medium is removed by use of suction filtration or a dryer. Then, the obtained starting material powders are placed in a container such as a crucible, followed by preliminary firing. The preliminary firing can be carried out at a temperature of, for example, 600 to 1,000° C. This can achieve homogeneous composition of the mixture and improvement in sintered density after sintering. However, the preliminary firing is not necessarily required. Instead, a compact preparation step mentioned below may be carried out using the starting material powders from which the dispersion medium has been removed by drying. On the other hand, the preliminary firing may be performed twice or more in order to improve homogeneity or sintered density.

In the case of performing the preliminary firing, preliminarily fired powders after the preliminary firing are ground again in the same way as in the grinding of the starting material powders using a grinding apparatus. In the grinding step following the preliminary firing, a binder or the like is added thereto at any of initial, intermediate, and final stages, followed by drying again to prepare starting material powders. For example, polyvinyl alcohol (PVA) or polyvinyl butyral (PVB) can be used as the binder.

Next, the obtained mixed powder of organic components and a ceramic is formed into cylindrical pellets of approximately 10 mm in diameter and approximately 1 mm in thickness to approximately 50 mm in diameter and approximately 5 mm in thickness using, for example, a press machine. Finally, the obtained compact is placed in an electric furnace and heated at 500 to 750° C. for a few hours to approximately 20 hours for binder removal treatment to obtain a starting material compact.

The starting material preparation step is described above with reference to the usual solid-phase method. However, the starting material preparation step is not limited by the solid-phase method and may be carried out by, for example, a hydrothermal synthesis method or a method using alkoxide as a starting material.

<Temperature Elevation Step>

Next, as illustrated in FIG. 18, the obtained starting material compact is placed again in a crucible or the like, and the temperature is elevated to the temperature of the first heat treatment step. The rate of temperature rise is not particularly limited and is usually set to 50 to 1,000° C./hr, though differing depending on the size of the starting material compact, the capacity of a heating apparatus, etc. For the purpose of removing water, for example, the temperature may be kept at 100 to 200° C. for a given time, or the rate of temperature rise may be slowed down. Such cases are also included in the temperature elevation step of the second aspect.

<First Heat Treatment Step>

Next, as illustrated in FIG. 18, the starting material compact is heat-treated at 800 to 1,150° C. When the piezoelectric composition of interest is a ceramic, the heat treatment time is 2 to 300 hours, more preferably 6 to 200 hours. In the case of obtaining a ceramic as the piezoelectric composition, this first heat treatment step serves as a sintering step for the starting material compact. This heat treatment time can be controlled to thereby control the particle size of the ceramic. As mentioned above, the ceramic obtained as the piezoelectric composition has a particle size of preferably 0.5 to 200 μm, more preferably 1 to 100 μm. This preferred particle size of the piezoelectric composition can be achieved by the heat treatment time (sintering time) set to 6 to 300 hours. The first heat treatment step may be carried out in air or may be carried out in an oxygen atmosphere or reductive atmosphere or in compositionally the same atmosphere (i.e., atmosphere where the compact is covered with preliminarily fired powders having the same composition thereas).

When the piezoelectric composition of interest is a single crystal, the heat treatment temperature is 2 to 3,000 hours, more preferably 6 to 3,000 hours. In the case of obtaining a single crystal as the piezoelectric composition, this first heat treatment step serves as a crystal growth step for the starting material compact.

<Temperature Lowering Step>

As mentioned later, the second heat treatment step serves as an annealing step. As illustrated in FIG. 18, the temperature lowering step therefore intervenes between the first heat treatment step and the second heat treatment step. The rate of temperature drop is not particularly limited and is usually set to 50 to 1,000° C./hr, though differing depending on the size of the starting material compact, the temperature lowering performance of a heating apparatus, etc.

<Second Heat Treatment Step>

Next, as illustrated in FIG. 18, the second heat treatment step is carried out for the starting material compact. This second heat treatment step serves as an annealing step. The annealing temperature is set to 300 to 900° C., more preferably 400 to 800° C. The annealing time is set to 5 minutes to 100 hours. This annealing step is carried out in order to remove various defects of the piezoelectric composition. In this context, the temperature of the second heat treatment step is set to be lower than the temperature of the first heat treatment step. This is because a second heat treatment temperature higher than the first heat treatment temperature further promotes sintering or melts the starting material compact. The annealing step may be carried out in air or may be carried out in an oxygen atmosphere, oxidative atmosphere (e.g., oxygen-nitrogen mixed gas atmosphere), or reductive atmosphere or in compositionally the same atmosphere (i.e., atmosphere where the compact is covered with preliminarily fired powders having the same composition thereas). For example, nitrogen gas, argon gas, or nitrogen-hydrogen mixed gas can be used as a reducing gas for the reductive atmosphere.

The annealing step may be carried out as a single round or may be carried out in two or more rounds at different temperatures. Specifically, the annealing step preferably involves heating at a first annealing temperature on the high temperature side, then temporal cooling to room temperature, and re-heating after temperature elevation to a second annealing temperature on the low temperature side. This is because various defects are removed at temperatures that are not the same among the defects. In the case of performing the annealing step in two rounds at different temperatures, the different temperatures are preferably 600 to 900° C. on the high temperature side and 300 to 600° C. on the low temperature side, more preferably 700 to 900° C. on the high temperature side and 400 to 600° C. on the low temperature side.

<Cooling Step>

Finally, as illustrated in FIG. 18, the compact thus heat-treated is cooled to room temperature. This cooling step is carried out in order to prevent various defects of the piezoelectric composition from gathering at domain walls. The rate of cooling is preferably 0.01 to 200° C./second, more preferably 5 to 100° C./second. A rate of cooling of 200° C./second or slower can be on the order of $1/10$ to $1/100$ or less of the rate of cooling in, for example, ultrahigh-speed quenching which involves dipping a compact having a temperature of 900° C. in hot water of 70° C. and thus, can avoid destroying the piezoelectric composition.

[Second Production Method]

Figure 19:
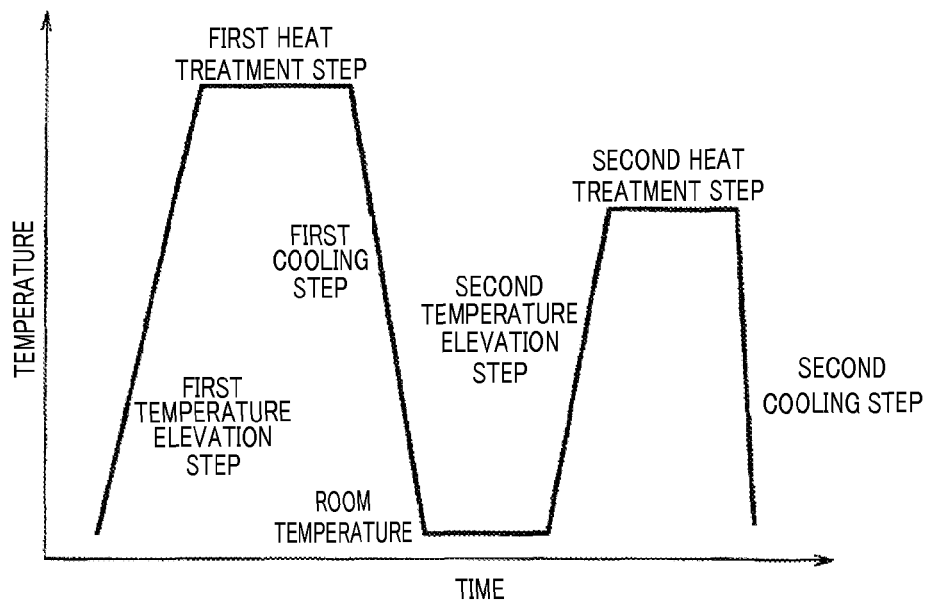
FIG. 19 schematically illustrates a second method for producing the lead-free piezoelectric element of the second aspect except for a starting material preparation step.

FIG. 19 schematically illustrates a second method for producing the lead-free piezoelectric element of the second aspect except for a starting material preparation step. The second method for producing the lead-free piezoelectric element of the second aspect includes a starting material preparation step, a first temperature elevation step, a first heat treatment step, a first cooling step, a second temperature elevation step, a second heat treatment step, and a second cooling step in the order presented to produce a piezoelectric composition contained in the lead-free piezoelectric element. Hereinafter, each step will be described.

<Starting Material Preparation Step>

The starting material preparation step in the second production method is carried out in the same way as in the starting material preparation step in the first production method.

<First Temperature Elevation Step>

As illustrated in FIG. 19, the first temperature elevation step in the second production method is carried out in the same way as in the temperature elevation step in the first production method.

<First Heat Treatment Step>

As illustrated in FIG. 19, the first heat treatment step in the second production method is carried out in the same way as in the first heat treatment step in the first production method.

<First Cooling Step>

Next, as illustrated in FIG. 19, the compact thus heat-treated is cooled to room temperature. The first cooling step can be carried out at substantially the same rate of cooling as that in the cooling step in the first production method. Although not shown in FIG. 19, the step of processing the compact after the first cooling step into a compact having a smaller shape may be additionally carried out. This enables the second heat treatment step (annealing step) mentioned later to be carried out for the compact having a smaller shape and consequently, can reliably prevent the piezoelectric composition from being destroyed by thermal shock in the second cooling step mentioned later. An electrode preparation step may be further carried out after the processing step.

<Second Temperature Elevation Step>

As mentioned later, the second heat treatment step serves as an annealing step. As illustrated in FIG. 19, the temperature elevation step is therefore carried out after the first cooling step. The rate of temperature rise is not particularly limited and can be set to, for example, 50 to 1,000° C./hr.

<Second Heat Treatment Step>

The second heat treatment step in the second production method serves as an annealing step. As illustrated in FIG. 19, the second heat treatment step in the second production method is carried out in the same way as in the second heat treatment step in the first production method. The annealing step may be carried out as a single round as in the second heat treatment step in the first production method or may be carried out in two or more rounds at different temperatures as in Example 2-9 mentioned later.

<Second Cooling Step>

As illustrated in FIG. 19, the second cooling step in the second production method is carried out in the same way as in the cooling step in the first production method.

Embodiment 2-3

Next, the ultrasonic probe of the second aspect will be described. The ultrasonic probe of the second aspect includes the lead-free piezoelectric element described in Embodiment 2-1.

Figure 20:
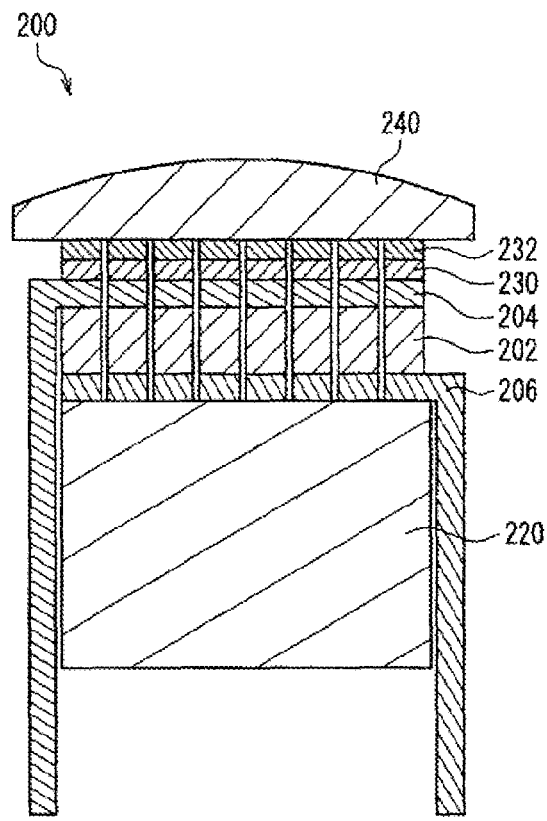
FIG. 20 is a cross-sectional view schematically illustrating the ultrasonic probe of the second aspect.

FIG. 20 is a cross-sectional view schematically illustrating the ultrasonic probe of the second aspect. The ultrasonic probe of the second aspect can be produced as follows: first, piezoelectric element 202 is temporarily polarized under desired polarization conditions. General piezoelectric element polarization conditions can be used as the polarization conditions. For example, piezoelectric element 202 is heated to 100 to 150° C. in an oil bath and kept for approximately 5 minutes to approximately 1 hour under conditions of 10 to 80 kV/cm. Then, the temperature of piezoelectric element 202 is lowered to room temperature to complete polarization. Next, piezoelectric element 202 (before cutting) thus completely polarized is fixed, using an electrically conductive adhesive or the like, onto lower lead electrode 206 fixed on back load material 220. Next, upper lead electrode 204 is also similarly bonded thereto using an electrically conductive adhesive or the like. First matching layer 230 and second matching layer 232 are further bonded and fixed thereonto. Next, in this state, the piezoelectric element is segmented using a dicing apparatus. For example, the piezoelectric element is cut into pitches of 200 to 400 μm in width. Acoustic lens 240 is further bonded thereto. After necessary casing (not shown), ultrasonic probe 200 can be produced.

The ultrasonic probe having the segmented piezoelectric element is described above. Alternatively, a single-plate ultrasonic probe may be used, as a matter of course.

Embodiment 2-4

Next, the diagnostic imaging apparatus of the second aspect will be described. The diagnostic imaging apparatus of the second aspect includes the ultrasonic probe described in Embodiment 2-3.

Figure 21:
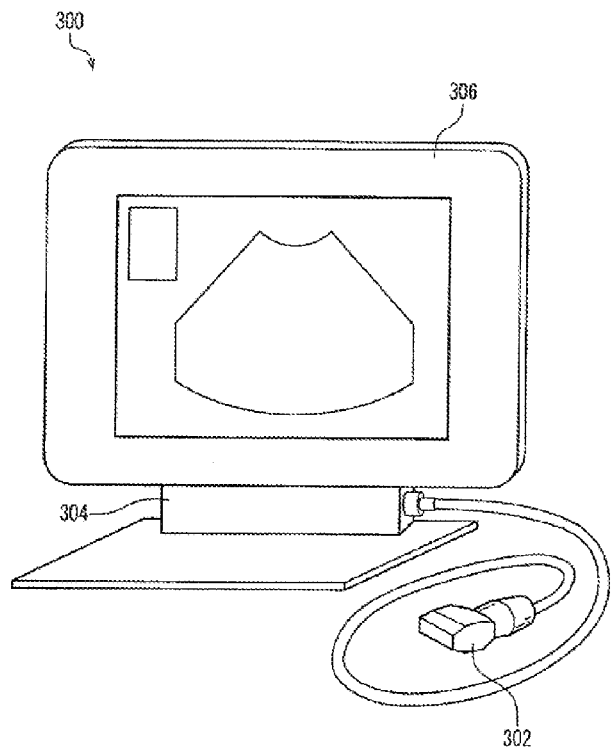
FIG. 21 is a perspective view schematically illustrating the diagnostic imaging apparatus of the second aspect.

FIG. 21 is a perspective view schematically illustrating the diagnostic imaging apparatus of the second aspect. In FIG. 21, ultrasonic diagnostic imaging apparatus 300 includes ultrasonic probe 302, ultrasonic diagnostic imaging apparatus body 304, and display 306. A conventional ultrasonic diagnostic apparatus body may be used as ultrasonic diagnostic imaging apparatus body 304 except for ultrasonic probe 302. In order to render the properties of ultrasonic diagnostic imaging apparatus body 304 consistent with ultrasonic probe 302 including the lead-free piezoelectric element, the signal processing circuit of ultrasonic diagnostic imaging apparatus body 304 and the electric impedance matching circuit of ultrasonic probe 302 can be adjusted to ones intended for ultrasonic probe 302. In order to apparently bring the electric impedance of ultrasonic probe 302 closer to the impedance of an ultrasonic probe including a conventional lead-based piezoelectric element, ultrasonic probe 302 may further include a circuit that finely adjusts impedance. Diagnostic imaging apparatus 300 can be used as a diagnostic imaging apparatus for specified diseases, for example, an ultrasonic diagnostic apparatus for intimal thickness measurement, or as an ultrasonic diagnostic imaging apparatus for other uses.

Hereinafter, the second aspect will be described with reference to Examples. However, the second aspect is not limited by Examples below.

Example 2-1

A piezoelectric element was prepared as mentioned below.
<Starting Material Preparation Step>
30 g in total of $Bi_2O_3$, $KHCO_3$, $TiO_2$, MgO, and $Fe_2O_3$ was weighed such that the composition of the resulting piezoelectric composition satisfied z=0.45 (x=0.45 and y=0.1) in compositional formula $x(Bi_{0.5}K_{0.5})TiO_3$-$yBi(Mg_{0.5}Ti_{0.5})O_3$-$zBiFeO_3$ to prepare starting materials. The starting materials used were reagents having a purity of 99.9 to 99.99%. Next, the weighed starting materials were placed in a pot together with ethanol and zirconia balls and ground for 16 hours using a ball mill. Then, the starting materials were dried. The starting material powders were further preliminarily fired at 800° C. for 6 hours. The obtained starting material powders were placed again in a pot together with ethanol and zirconia balls and ground again for 16 hours using a ball mill. Then, PVB was added thereto as a binder, followed by drying. Next, a pressure of approximately 200 to 250 MPa was applied to the obtained starting material powders using a uniaxial press apparatus to prepare pellets of 10 mm in diameter and 1.5 mm in thickness. The obtained pellets were heated at 700° C. for 10 hours for removal of the binder to obtain a starting material compact.

<Temperature Elevation Step>
Next, the temperature of the obtained starting material compact was elevated to 1,000° C. at a rate of temperature rise of 300° C./hr.

<First Heat Treatment Step>
Next, the starting material compact was sintered at 1,000° C. for 2 hours.

<Temperature Lowering Step>
Next, the temperature of the compact thus sintered was lowered to 800° C. at a rate of 300° C./hr.

<Second Heat Treatment Step (Annealing Step)>
Subsequently, the temperature-lowered compact was annealed at 800° C. for 20 hours.

<Cooling Step>
Finally, the compact thus annealed was cooled to room temperature at a rate of cooling of 40 to 100° C./second to obtain a piezoelectric composition.

Next, the obtained piezoelectric composition was processed into a thickness of approximately 0.4 mm by polishing. Then, gold electrodes were formed on both sides of the piezoelectric composition by sputtering to obtain a piezoelectric element. The surface resistance of the electrodes in the prepared piezoelectric element was measured with 2 mm spacing between the terminals and consequently confirmed to be as favorable as a few ohms or less.

Subsequently, the dielectric properties and piezoelectric properties of the prepared piezoelectric element were measured.

Figure 22:
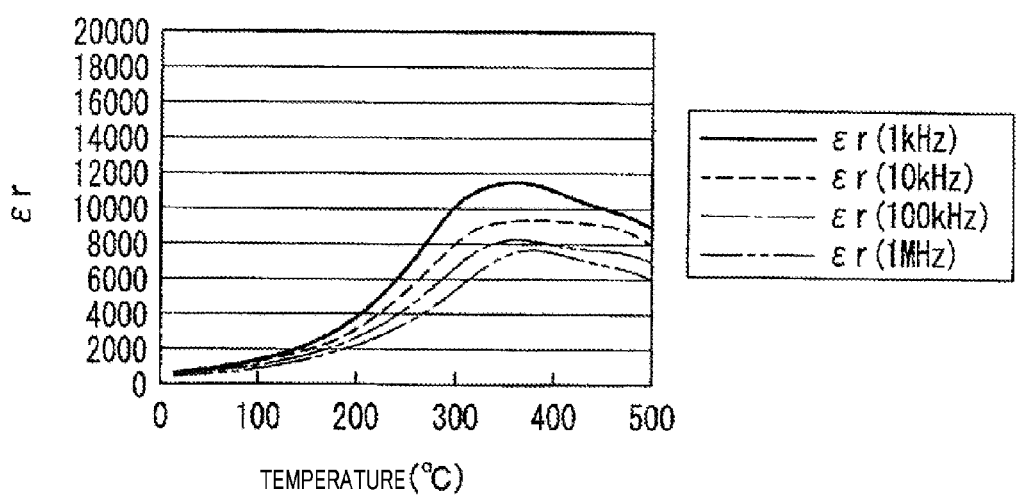
FIG. 22 illustrates the relationship between the relative permittivity of a piezoelectric element of Example 2-1 according to the second aspect and a temperature.
Figure 23:
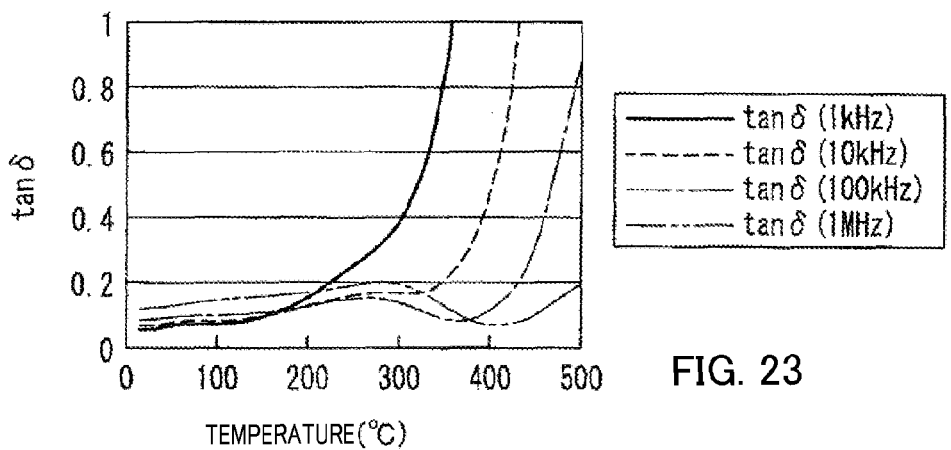
FIG. 23 illustrates the relationship between the dielectric loss of the piezoelectric element of Example 2-1 according to the second aspect and a temperature.

First, the relative permittivity and dielectric loss of the prepared piezoelectric element were measured as dielectric properties using an LCR meter (model 6440B) manufactured by Wayne Kerr Electronics. FIG. 22 illustrates the temperature characteristics of relative permittivity of the piezoelectric element. FIG. 23 illustrates the temperature characteristics of dielectric loss of the piezoelectric element. Since dielectric loss (tan δ) becomes large (1 or larger) at a temperature elevated to 500° C. at a low frequency, the relative permittivity and the dielectric loss were evaluated at 1 MHz in this study. As a result, the piezoelectric element had a relative permittivity ∈r of 430 and a dielectric loss tan δ of 0.12 at 25° C. Also, the piezoelectric element had a relative permittivity ∈m of 7,700 and a dielectric loss tan δ of 0.09 at maximum temperature Tm (376° C.).

Figure 24:
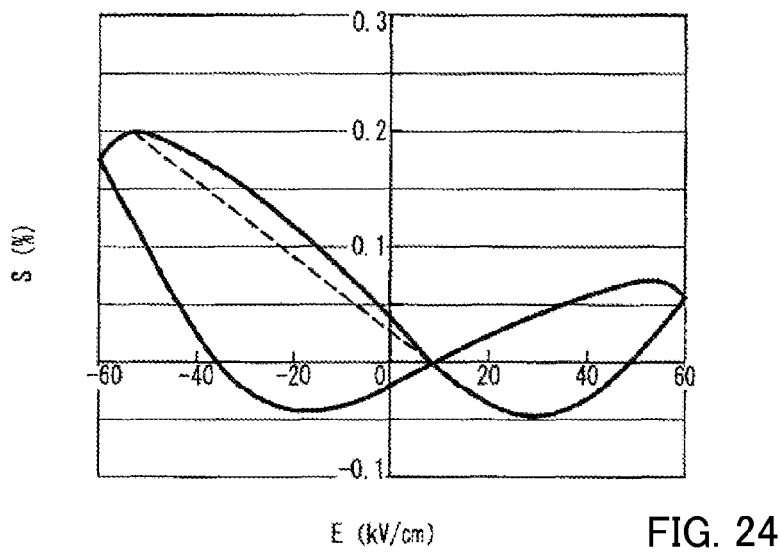
FIG. 24 illustrates the electric field-strain properties of the piezoelectric element of Example 2-1 according to the second aspect.
Figure 25:
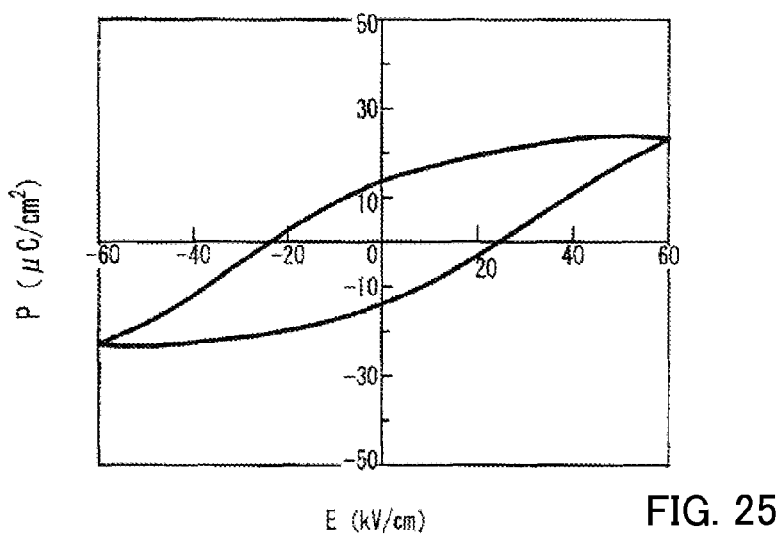
FIG. 25 illustrates the electric field-polarization properties of the piezoelectric element of Example 2-1 according to the second aspect.

Next, the electric field-strain properties and electric field-polarization properties of the prepared piezoelectric element were measured as piezoelectric properties by use of a ferroelectric evaluation system "FCE-3" manufactured by TOYO Corp. or a self-made measurement system using a contact-type displacement gauge and an integrator. This measurement of the piezoelectric properties was performed after calibration with the value of commercially available PZT having a known piezoelectric constant d33* and remnant polarization. FIG. 24 illustrates the electric field-strain properties of the piezoelectric element. FIG. 25 illustrates the electric field-polarization properties of the piezoelectric element. The piezoelectric element had a piezoelectric constant d33* of 331 pm/V determined from FIG. 24 and a remnant polarization Pr of 13.6 µC/cm$^2$ determined from FIG. 25, and thus exhibited great piezoelectric properties as a lead-free piezoelectric element, though asymmetry was seen in the electric field-strain properties.

The piezoelectric composition in the piezoelectric element was observed under a scanning electron microscope (SEM). As a result, the piezoelectric composition (ceramic) had a particle size of 0.5 to 1.5 µm.

Example 2-2

A piezoelectric element was prepared as mentioned below.
<Starting Material Preparation Step>
A starting material compact was prepared in the same way as in Example 2-1.
<Temperature Elevation Step>
Next, the temperature of the obtained starting material compact was elevated to 1,000° C. at a rate of temperature rise of 100° C./hr.
<First Heat Treatment Step>
Next, the starting material compact was sintered at 1,000° C. for 20 hours.
<Temperature Lowering Step>
Next, the temperature of the compact thus sintered was lowered to 800° C. at a rate of 100° C./hr.
<Second Heat Treatment Step (Annealing Step)>
Subsequently, the temperature-lowered compact was annealed at 800° C. for 20 hours.
<Cooling Step>
Finally, the compact thus annealed was cooled to room temperature at a rate of cooling of 40 to 100° C./second to obtain a piezoelectric composition.

Next, the obtained piezoelectric composition was processed into a thickness of approximately 0.4 mm by polishing. Then, gold electrodes were formed on both sides of the piezoelectric composition by sputtering to obtain a piezoelectric element. The surface resistance of the electrodes in the prepared piezoelectric element was measured with 2 mm spacing between the terminals and consequently confirmed to be as favorable as a few ohms or less.

Figure 26:
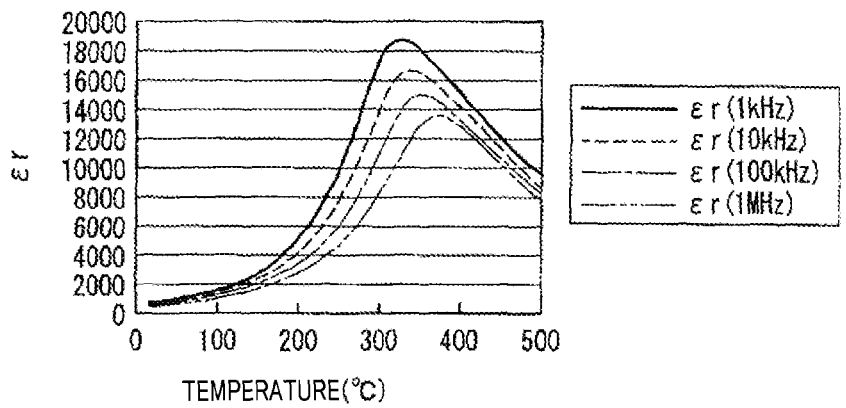
FIG. 26 illustrates the relationship between the relative permittivity of a piezoelectric element of Example 2-2 according to the second aspect and a temperature.
Figure 27:
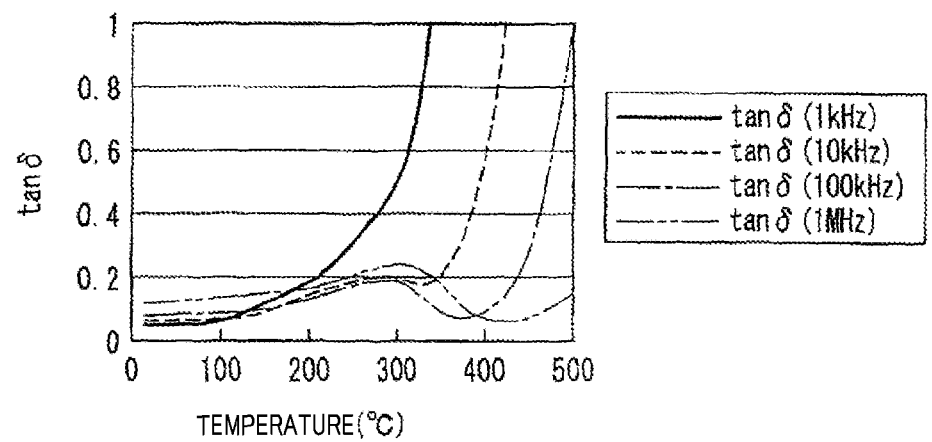
FIG. 27 illustrates the relationship between the dielectric loss of the piezoelectric element of Example 2-2 according to the second aspect and a temperature.

Subsequently, the dielectric properties and piezoelectric properties of the prepared piezoelectric element were measured in the same way as in Example 2-1. FIG. 26 illustrates the temperature characteristics of relative permittivity of the piezoelectric element. FIG. 27 illustrates the temperature characteristics of dielectric loss of the piezoelectric element. As a result, the piezoelectric element had a relative permittivity ∈r of 491 and a dielectric loss tan δ of 0.11 at 25° C. Also, the piezoelectric element had a relative permittivity ∈m of 13,500 and a dielectric loss tan δ of 0.12 at maximum temperature Tm (371° C.).

Figure 28:
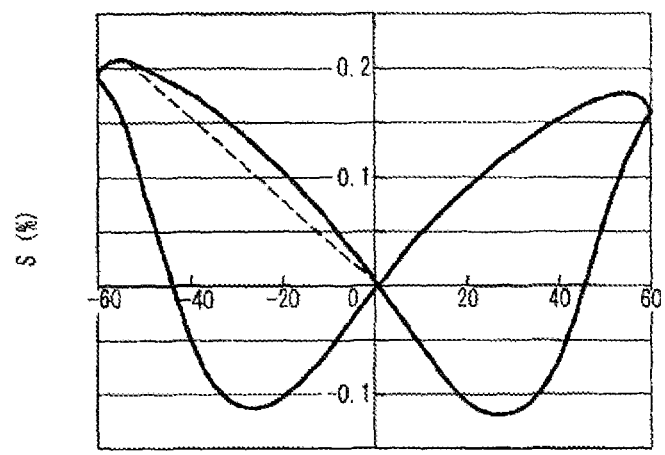
FIG. 28 illustrates the electric field-strain properties of the piezoelectric element of Example 2-2 according to the second aspect.
Figure 29:
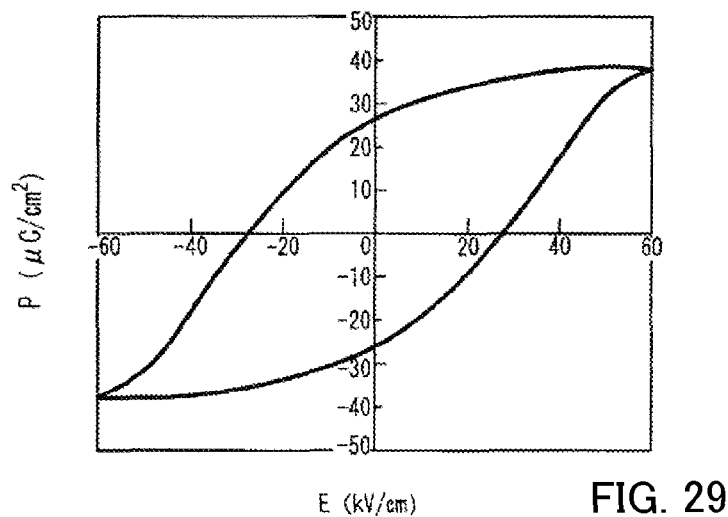
FIG. 29 illustrates the electric field-polarization properties of the piezoelectric element of Example 2-2 according to the second aspect.

FIG. 28 illustrates the electric field-strain properties of the piezoelectric element. FIG. 29 illustrates the electric field-polarization properties of the piezoelectric element. The piezoelectric element had a piezoelectric constant d33* of 378 pm/V determined from FIG. 28 and a remnant polarization Pr of 27 µC/cm$^2$ determined from FIG. 29, and thus exhibited great piezoelectric properties as a lead-free piezoelectric element.

The piezoelectric composition in the piezoelectric element was observed under a scanning electron microscope (SEM). As a result, the piezoelectric composition (ceramic) had a particle size of 2 to 5 µm.

In this Example, the longer sintering time than that of Example 2-1 was able to increase both relative permittivity ∈r and remnant polarization Pr compared with those of Example 2-1.

Example 2-3

A piezoelectric element was prepared in the same way as in Example 2-2 except that the sintering time of the first heat treatment step was set to 200 hours. Next, the dielectric properties and piezoelectric properties of the prepared piezoelectric element were measured in the same way as in Example 2-1. As a result, the piezoelectric element had a relative permittivity ∈r of 490 and a dielectric loss tan δ of 0.08 at 25° C., and had a relative permittivity ∈m of 14,000 and a dielectric loss tan δ of 0.12 at maximum temperature Tm (370° C.). Also, the piezoelectric element had a piezoelectric constant d33* of 410 pm/V and a remnant polarization Pr of 27 µC/cm$^2$.

The piezoelectric composition in the piezoelectric element was observed under a scanning electron microscope (SEM). As a result, the piezoelectric composition (ceramic) had a particle size of 3 to 10 µm.

Example 2-4

A piezoelectric element was prepared in the same way as in Example 2-2 except that the sintering time of the first heat treatment step was set to 300 hours. Next, the dielectric properties and piezoelectric properties of the prepared piezoelectric element were measured in the same way as in Example 2-1 and were almost similar to the results of Example 2-3.

Comparative Example 2-1

A piezoelectric element was prepared as mentioned below.
<Starting Material Preparation Step>
A starting material compact was prepared in the same way as in Example 2-1.
<Temperature Elevation Step>
Next, the temperature of the obtained starting material compact was elevated to 1,000° C. at a rate of temperature rise of 300° C./hr.
<First Heat Treatment Step>
Subsequently, the starting material compact was sintered at 1,000° C. for 2 hours.
<Temperature Lowering Step>
The temperature lowering step was not carried out.
<Second Heat Treatment Step (Annealing Step)>
The second heat treatment step was not carried out.
<Cooling Step>
Finally, the compact thus sintered was cooled to room temperature at a rate of cooling of 0.055° C./second to obtain a piezoelectric composition.

Next, the obtained piezoelectric composition was processed into a thickness of approximately 0.4 mm by polishing. Then, gold electrodes were formed on both sides of the piezoelectric composition by sputtering to obtain a piezoelectric element.

Figure 30:
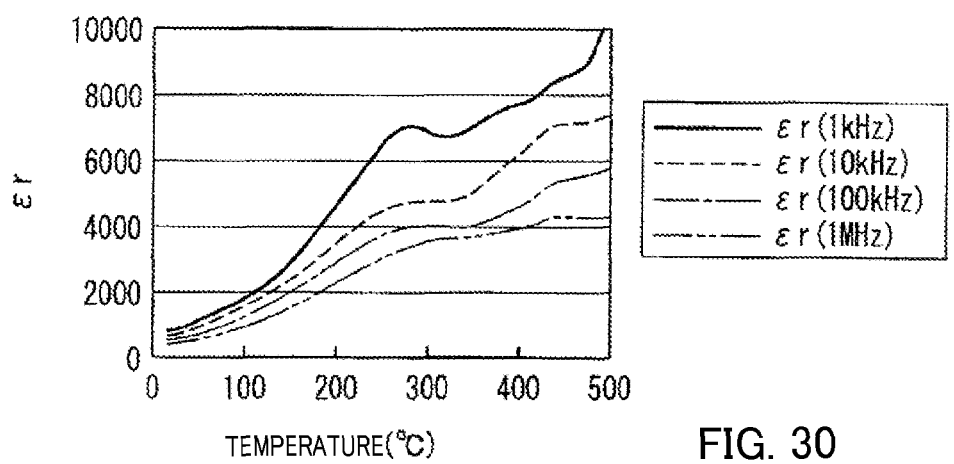
FIG. 30 illustrates the relationship between the relative permittivity of a piezoelectric element of Comparative Example 2-1 and a temperature.
Figure 31:
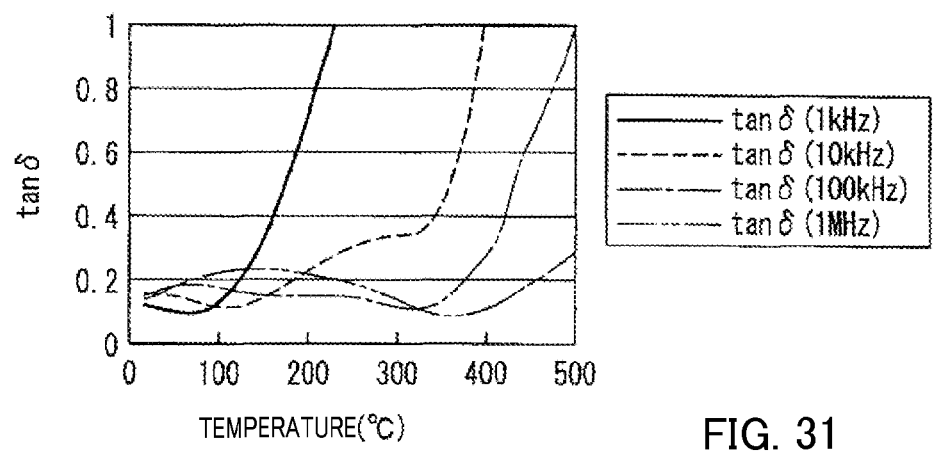
FIG. 31 illustrates the relationship between the dielectric loss of the piezoelectric element of Comparative Example 2-1 and a temperature.

Subsequently, the dielectric properties and piezoelectric properties of the prepared piezoelectric element were measured in the same way as in Example 2-1. FIG. 30 illustrates the temperature characteristics of relative permittivity of the piezoelectric element. FIG. 31 illustrates the temperature characteristics of dielectric loss of the piezoelectric element. As a result, the piezoelectric element had a relative permittivity $\in r$ of 440 and a dielectric loss tan δ of 0.14 at 25° C. Also, the piezoelectric element had a relative permittivity $\in m$ of 3,590 and a dielectric loss tan δ of 0.13 at maximum temperature Tm (305° C.).

Figure 32:
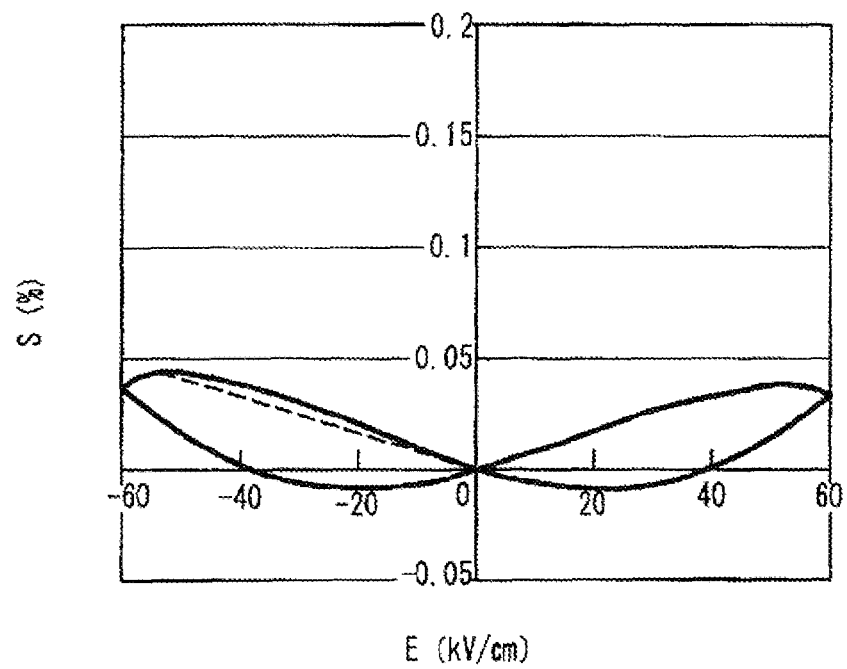
FIG. 32 illustrates the electric field-strain properties of the piezoelectric element of Comparative Example 2-1.
Figure 33:
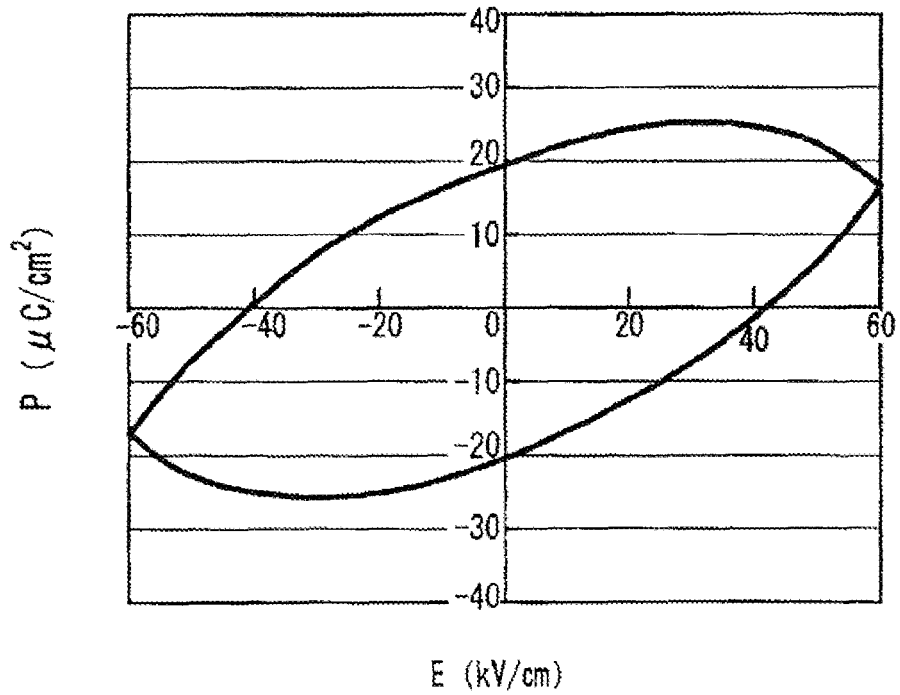
FIG. 33 illustrates the electric field-polarization properties of the piezoelectric element of Comparative Example 2-1.

FIG. 32 illustrates the electric field-strain properties of the piezoelectric element. FIG. 33 illustrates the electric field-polarization properties of the piezoelectric element. The piezoelectric element had a piezoelectric constant d33* of 84 pm/V determined from FIG. 32, and its remnant polarization Pr determined from FIG. 33 was not accurately measurable due to leak current.

Example 2-5

A piezoelectric composition was prepared as mentioned below.

<Starting Material Preparation Step>

A starting material compact was prepared in the same way as in Example 2-1 except that the size of the starting material compact was set to 50 mm in diameter and 5 mm in thickness.

<First Temperature Elevation Step>

Next, the temperature of the obtained starting material compact was elevated to 1,000° C. at a rate of temperature rise of 100° C./hr.

<First Heat Treatment Step>

Next, the starting material compact was sintered at 1,000° C. for 20 hours.

<First Cooling Step>

Next, the compact thus sintered was cooled from 1,000° C. to room temperature over 12 hours.

<Processing Step>

Next, the temperature-lowered compact was abrasively cut and processed into a compact of 15 mm in diameter and 3 mm in thickness.

<Second Temperature Elevation Step>

Next, the temperature of the processed compact was elevated to 800° C. over 2 hours and 40 minutes.

<Second Heat Treatment Step (Annealing Step)>

Next, the temperature-elevated compact was annealed at 800° C. for 20 hours.

<Second Cooling Step>

Finally, the compact thus annealed was cooled to room temperature at a rate of cooling of 40 to 100° C./second to obtain a piezoelectric composition.

Next, the obtained piezoelectric composition was processed into a diameter of 13 mm and a thickness of 1 mm by polishing. Then, gold electrodes were formed on both sides of the piezoelectric composition by sputtering to obtain a piezoelectric element.

Next, the dielectric properties and piezoelectric properties of the prepared piezoelectric element were measured in the same way as in Example 2-1. As a result, the piezoelectric element had a relative permittivity $\in r$ of 460 and a dielectric loss tan δ of 0.11 at 25° C., and had a relative permittivity $\in m$ of 12,500 and a dielectric loss tan δ of 0.12 at maximum temperature Tm (371° C.). Also, the piezoelectric element had a piezoelectric constant d33* of 360 pm/V and a remnant polarization Pr of 24 μC/cm².

Example 2-6

A piezoelectric composition was prepared as mentioned below.

<Starting Material Preparation Step>

A starting material compact was obtained in the same way as in the starting material preparation step of Example 2-1 except that 30 g in total of $Bi_2O_3$, $KHCO_3$, $TiO_2$, MgO, and $Fe_2O_3$ was weighed such that the composition of the resulting piezoelectric composition satisfied z=0.4 (x=0.5 and y=0.1) in compositional formula $x(Bi_{0.5}K_{0.5})TiO_3$-$yBi(Mg_{0.5}Ti_{0.5})O_3$-$zBiFeO_3$ to prepare starting materials.

<Temperature Elevation Step>

Next, the temperature of the obtained starting material compact was elevated to 1,000° C. at a rate of temperature rise of 300° C./hr.

<First Heat Treatment Step>

Next, the starting material compact was sintered at 1,000° C. for 2 hours.

<Temperature Lowering Step>

Next, the temperature of the compact thus sintered was lowered to 800° C. at a rate of 100° C./hr.

<Second Heat Treatment Step (Annealing Step)>

Subsequently, the temperature-lowered compact was annealed at 800° C. for 20 hours.

<Cooling Step>

Finally, the compact thus annealed was cooled to room temperature at a rate of cooling of 40 to 100° C./second to obtain a piezoelectric composition.

Next, a piezoelectric element was prepared in the same way as in Example 2-1. The piezoelectric constant d33* of the prepared piezoelectric element was measured in the same way as in Example 2-1. In addition, piezoelectric elements were prepared in the same way as above except that: the amount z of BFO (molar ratio) in the compositional formula was changed to 0.1 to 0.85 (in this context, x=0.9−z and y=0.1); the sintering temperature of the first heat treatment step was changed to 900 to 1,065° C. to achieve the largest sintered density; and the rate of cooling in the cooling step was changed to 40 to 100° C./second. The piezoelectric constants d33* of the prepared piezoelectric elements were measured in the same way as in Example 2-1. These results are indicated by mark ● in FIG. 34.

Example 2-7

A piezoelectric composition was prepared in the same way as in Example 2-6 except that the sintering time of the first heat treatment step was set to 20 hours. Next, a piezoelectric element was prepared in the same way as in Example 2-1. The piezoelectric constant d33* of the prepared piezoelectric element was measured in the same way as in Example 2-1. In addition, piezoelectric elements were prepared in the same way as above except that the amount z of BFO (molar ratio) in the compositional formula shown in the starting material preparation step of Example 2-6 was changed to 0.4 to 0.5 (in this context, x=0.9−z and y=0.1). The piezoelectric constants d33* of the prepared piezoelectric elements were measured in the same way as in Example 2-1. These results are indicated by mark □ in FIG. 34.

Comparative Example 2-2

A piezoelectric composition was prepared in the same way as in Example 2-6 except that the sintered compact was cooled over 5 hours in the cooling step without the temperature lowering step and the second heat treatment step (annealing step). Next, a piezoelectric element was prepared in the same way as in Example 2-1. The piezoelectric constant d33* of the prepared piezoelectric element was measured in the same way as in Example 2-1. In addition, piezoelectric elements were prepared in the same way as above except that the amount z of BFO (molar ratio) in the compositional formula shown in the starting material preparation step of Example 2-6 was changed to 0.05 to 0.85 (in this context, x=0.9−z and y=0.1). The piezoelectric constants d33* of the prepared piezoelectric elements were measured in the same way as in Example 2-1. These results are indicated by mark ♦ in FIG. 34.

Comparative Example 2-3

Piezoelectric compositions in which z=0.4 to 0.6 (x=0.9−z and y=0.1) were prepared in the same way as in Comparative Example 2-1 without the temperature lowering step and the second heat treatment step (annealing step). In addition, piezoelectric compositions were prepared in the same way as in Comparative Example 2-1 except that, as in conventional cases, the piezoelectric compositions were annealed at 900° C. for 5 minutes and then dipped in water of 70° C. (the rate of cooling in this procedure was approximately 830° C./second or faster). In this approach, some piezoelectric compositions were destroyed. From among undestroyed piezoelectric compositions, piezoelectric elements were prepared in the same way as in Example 2-1. Next, the piezoelectric constants d33* of the prepared piezoelectric elements were measured in the same way as in Example 2-1. These results are indicated by mark A in FIG. 34.

Figure 34:
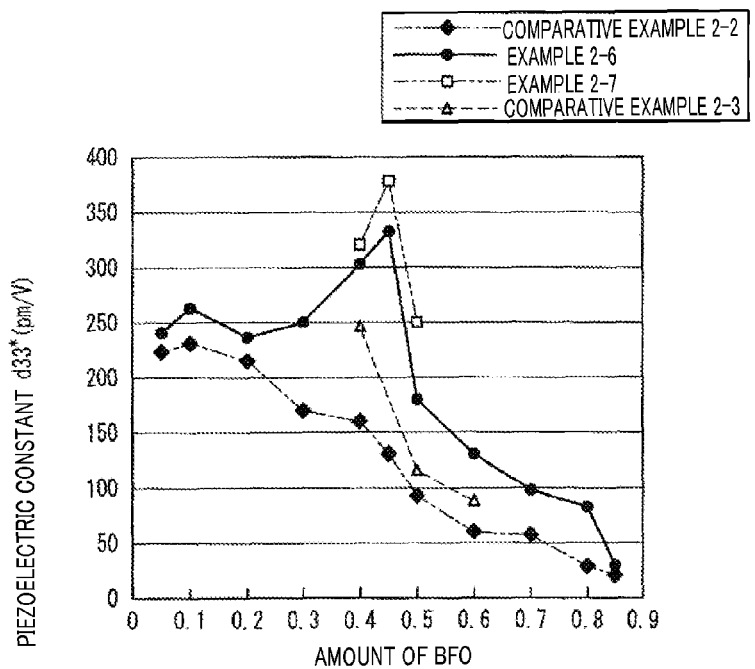
FIG. 34 illustrates the relationship between the amount of BFO and d33*.

As is evident from FIG. 34, the piezoelectric constants d33* of Examples 2-6 and 2-7 involving the annealing step reached a peak when the amount z of BFO (molar ratio) was 0.45. As is also evident, the piezoelectric constant d33* of Example 2-6 was increased even when the amount z of BFO (molar ratio) was 0.1. The crystal structure of the piezoelectric compositions of Example 2-6 were analyzed by powder X-ray diffraction. As a result, the composition in which z=0.1 was confirmed to be in proximity to a tetragonal-pseudocubic phase boundary. X-ray diffraction results of the piezoelectric compositions prepared separately and results about piezoelectric elements prepared using the piezoelectric compositions demonstrated that a tetragonal-pseudocubic phase boundary exists, for example, in x=0.92, y=0.04, and z=0.04. The composition in which z=0.45 was confirmed to include a rhombohedral-pseudocubic phase boundary.

Next, the influence of an additive on the piezoelectric element of the second aspect will be described.

Example 2-8

A piezoelectric element was prepared as mentioned below.
<Starting Material Preparation Step>
A starting material compact was prepared in the same way as in the starting material preparation step of Example 2-1 except that: the starting materials used were 30 g in total of $Bi_2O_3$, $KHCO_3$, $TiO_2$, MgO, and $Fe_2O_3$ weighed such that the composition of the resulting piezoelectric composition satisfied z=0.45 (x=0.45 and y=0.1) in compositional formula $x(Bi_{0.5}K_{0.5})TiO_3$-$yBi(Mg_{0.5}Ti_{0.5})O_3$-$zBiFeO_3$; and 0.1 wt % (0.03 g) of $MnCO_3$ was further added to this 30 g of the starting materials to prepare starting materials.

<First Temperature Elevation Step>
Next, the temperature of the obtained starting material compact was elevated to 1,000° C. at a rate of temperature rise of 300° C./hr.

<First Heat Treatment Step>
Next, the starting material compact was sintered at 1,000° C. for 20 hours.

<First Cooling Step>
Next, the compact thus sintered was cooled to room temperature at a rate of cooling of 300° C./hr.

<Second Temperature Elevation Step>
Next, the temperature of the cooled compact was elevated to 800° C. at a rate of temperature rise of 300° C./hr.

<Second Heat Treatment Step (Annealing Step)>
Next, the temperature-elevated compact was annealed at 800° C. for 20 hours.

<Second Cooling Step>
Finally, the compact thus annealed was cooled to room temperature at a rate of cooling of 40 to 100° C./second to obtain a piezoelectric composition.

Next, the obtained piezoelectric composition was processed into a thickness of approximately 0.4 mm by polishing and then cut into a size of 4 mm long and 1.5 mm wide. Gold electrodes were formed on both sides of the piezoelectric element by sputtering to obtain a piezoelectric element as illustrated in FIG. 16.

Figure 35:
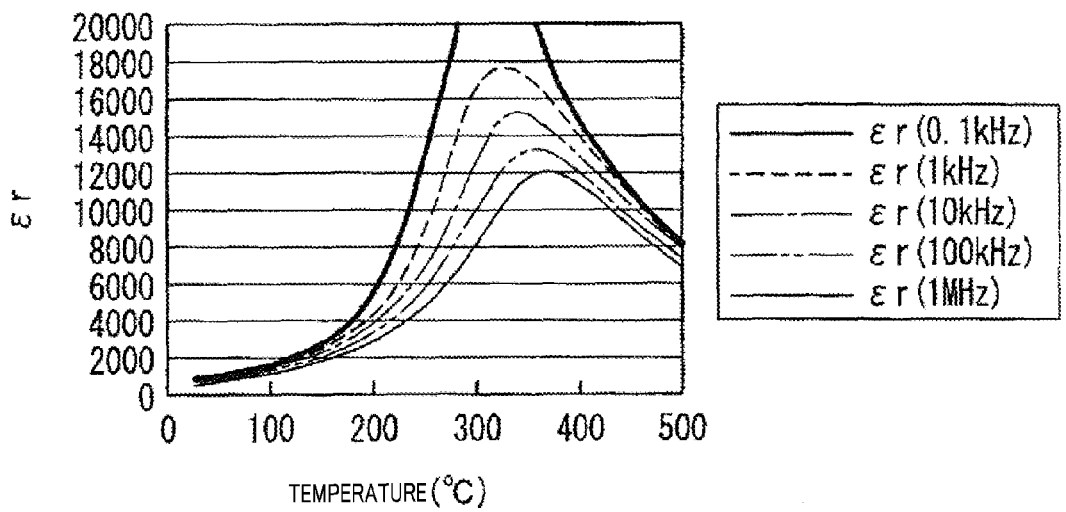
FIG. 35 illustrates the relationship between the relative permittivity of a piezoelectric element of Example 2-8 according to the second aspect and a temperature.
Figure 36:
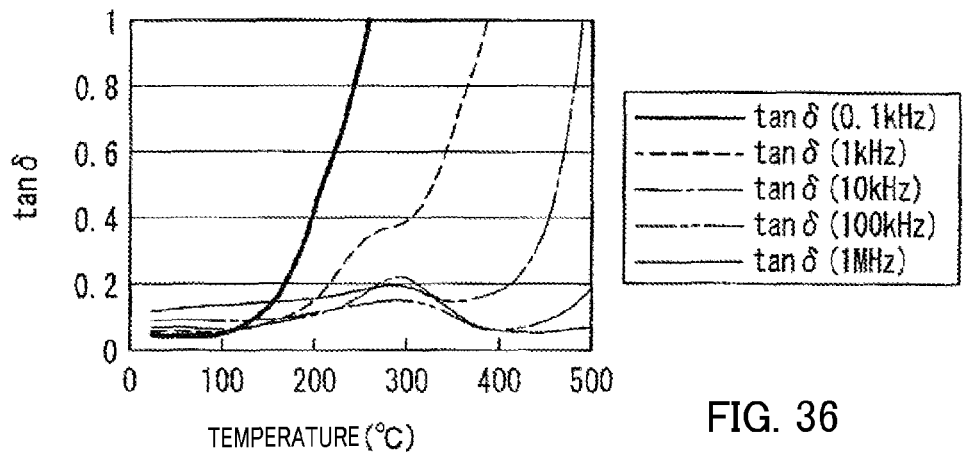
FIG. 36 illustrates the relationship between the dielectric loss of the piezoelectric element of Example 2-8 according to the second aspect and a temperature.

Subsequently, the dielectric properties and piezoelectric properties of the prepared piezoelectric element were measured in the same way as in Example 2-1. FIG. 35 illustrates the temperature characteristics of relative permittivity of the piezoelectric element. FIG. 36 illustrates the temperature characteristics of dielectric loss of the piezoelectric element. As a result, the piezoelectric element had a relative permittivity ∈r of 483 and a dielectric loss tan δ of 0.12 at 25° C. Also, the piezoelectric element had a relative permittivity ∈m of 12,000 and a dielectric loss tan δ of 0.09 at maximum temperature Tm (367° C.). The piezoelectric element had a piezoelectric constant d33* of 372 pm/V and a remnant polarization Pr of 24 µC/cm², and thus exhibited great piezoelectric properties as a lead-free piezoelectric element. In order to evaluate insulation properties at high temperatures having a great impact on polarization treatment, the dielectric loss tan δ was measured at a temperature of 150° C. and 100 Hz and consequently confirmed to be 0.13, indicating relatively low loss.

Example 2-9

Figure 37:
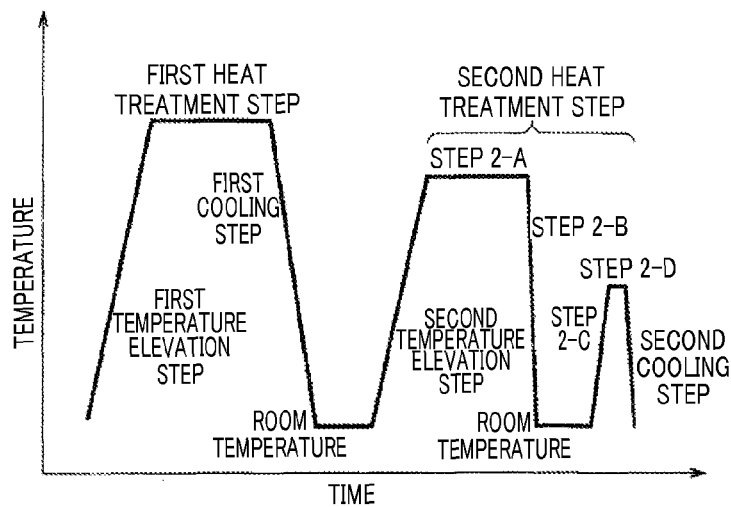
FIG. 37 schematically illustrates a method for producing a piezoelectric element of Example 2-9 except for a starting material preparation step.

A piezoelectric element was prepared in the same way as in Example 2-8 except that the second heat treatment step and the second cooling step were changed as described below. FIG. 37 schematically illustrates a method for producing the piezoelectric element of this Example except for a starting material preparation step.

<Second Heat Treatment Step (Annealing Step)>
In this Example, the annealing step was carried out in 2 stages (first annealing step and second annealing step) as described below.

(First Annealing Step; which is Indicated as Step 2-A in FIG. 37)

The compact after the second temperature elevation step was annealed at 800° C. for 20 hours.

(Cooling Step; which is Indicated as Step 2-B in FIG. 37)

Next, the compact after the first annealing step was cooled to room temperature at a rate of cooling of 40 to 100° C./second.

(Temperature Elevation Step; which is Indicated as Step 2-C in FIG. 37)

Next, the temperature of the compact thus cooled was elevated to 500° C. at a rate of temperature rise of 250° C./hr.

(Second Annealing Step; which is Indicated as Step 2-D in FIG. 37)

Next, the temperature-elevated compact was annealed at 500° C. for 10 minutes.

<Second Cooling Step>

Finally, the compact after the second annealing was cooled to room temperature at a rate of cooling of 200 to 300° C./hr (0.06 to 0.08° C./second) to obtain a piezoelectric composition.

Figure 38:
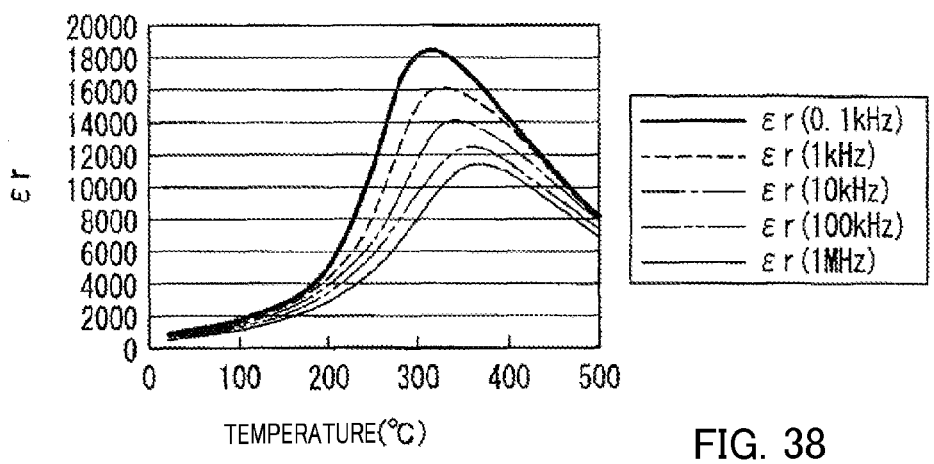
FIG. 38 illustrates the relationship between the relative permittivity of a piezoelectric element of Example 2-9 according to the second aspect and a temperature.
Figure 39:
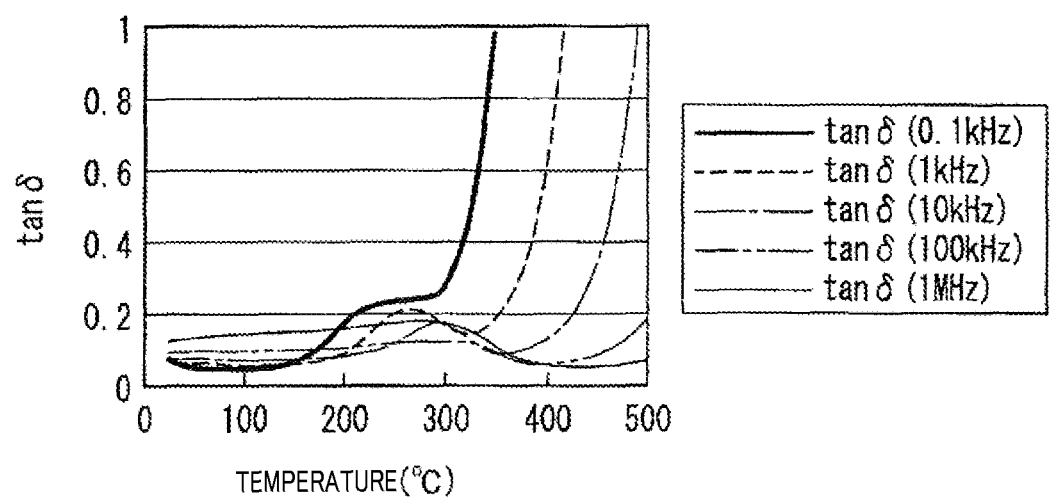
FIG. 39 illustrates the relationship between the dielectric loss of the piezoelectric element of Example 2-9 according to the second aspect and a temperature.

Next, the dielectric properties and piezoelectric properties of the prepared piezoelectric element were measured in the same way as in Example 2-1. FIG. 38 illustrates the temperature characteristics of relative permittivity of the piezoelectric element. FIG. 39 illustrates the temperature characteristics of dielectric loss of the piezoelectric element. As a result, the piezoelectric element had a relative permittivity $\in r$ of 493 and a dielectric loss tan δ of 0.12 at 25° C. Also, the piezoelectric element had a relative permittivity $\in m$ of 11,400 and a dielectric loss tan δ of 0.08 at maximum temperature Tm (367° C.). The piezoelectric element had a piezoelectric constant d33* of 370 pm/V and a remnant polarization Pr of 21 µC/cm$^2$, and thus exhibited great piezoelectric properties as a lead-free piezoelectric element. In order to evaluate insulation properties at high temperatures having a great impact on polarization treatment, the dielectric loss tan δ was measured at a temperature of 150° C. and 100 Hz and consequently confirmed to be 0.06 which was lower than half the dielectric loss tan δ of Example 2-8, indicating very low loss.

Table 6 shows typical characteristic values of the piezoelectric elements of Examples 2-8 and 2-9.

TABLE 6

| | Example 2-8 | Example 2-9 |
|---|---|---|
| Piezoelectric constant d33* (pm/V) | 372 | 370 |
| Remnant polarization Pr (µC/cm$^2$) | 24 | 21 |
| Relative permittivity $\in m$ (1 MHz) | 12,000 | 11,400 |
| Dielectric loss tanδ (1 MHz) | 0.09 | 0.08 |
| Dielectric loss tanδ (100 Hz, 150° C.) | 0.13 | 0.06 |

Although the details are unknown, the results described above demonstrated that the addition of Mn in a trace amount and the 2-stage second heat treatment step (annealing step) are particularly effective for reduction in the loss of the piezoelectric element, which cannot be achieved by simple procedures of Mn addition and sintering.

The influence of an additive on the piezoelectric element of the second aspect is described above with reference to cases using MnCO$_3$ added in an amount of 0.1 wt %. MnCO$_3$ added in an amount on the order of 0.05 to 0.3 wt % produces almost similar effects. The Mn additive used in Example 2-8 or 2-9 was MnCO$_3$. Likewise, other Mn additives such as MnO, Mn$_2$O$_3$, Mn$_3$O$_4$, and MnO$_2$ are also effective.

Next, the influence of heat treatment in a reductive atmosphere on the piezoelectric element of the second aspect will be described.

Example 2-10

A piezoelectric element was prepared as mentioned below.

<Starting Material Preparation Step>

A starting material compact was prepared in the same way as in the starting material preparation step of Example 2-1 except that: the starting materials used were 30 g in total of Bi$_2$O$_3$, KHCO$_3$, TiO$_2$, MgO, and Fe$_2$O$_3$ weighed such that the composition of the resulting piezoelectric composition satisfied z=0.523 (x=0.427 and y=0.05) in compositional formula x(Bi$_{0.5}$K$_{0.5}$)TiO$_3$-yBi(Mg$_{0.5}$Ti$_{0.5}$)O$_3$-zBiFeO$_3$; and 0.1 wt % (0.03 g) of MnCO$_3$ was further added to this 30 g of the starting materials to prepare starting materials.

<First Temperature Elevation Step>

Next, the temperature of the obtained starting material compact was elevated to 1,000° C. at a rate of temperature rise of 300° C./hr.

<First Heat Treatment Step>

Next, the starting material compact was sintered at 1,000° C. for 20 hours.

<First Cooling Step>

Next, the compact thus sintered was cooled to room temperature at a rate of cooling of 300° C./hr.

<Second Temperature Elevation Step>

Next, the temperature of the cooled compact was elevated to 800° C. at a rate of temperature rise of 300° C./hr in a nitrogen atmosphere.

<Second Heat Treatment Step (Annealing Step)>

Next, the temperature-elevated compact was annealed at 800° C. for 20 hours in a nitrogen atmosphere.

<Second Cooling Step>

Finally, the compact thus annealed was cooled to room temperature at a rate of cooling of 0.01 to 0.05° C./second in a nitrogen atmosphere to obtain a piezoelectric composition.

Next, the obtained piezoelectric composition was processed into a thickness of approximately 0.4 mm by polishing and then cut into a size of 4 mm long and 1.5 mm wide. Gold electrodes were formed on both sides of the piezoelectric element by sputtering to obtain a piezoelectric element as illustrated in FIG. 16.

Subsequently, the dielectric properties and piezoelectric properties of the prepared piezoelectric element were measured in the same way as in Example 2-1. As a result, the piezoelectric element had a relative permittivity $\in r$ of 460 and a dielectric loss tan δ of 0.11 at 25° C. Also, the piezoelectric element had a relative permittivity $\in m$ of 11,400 and a dielectric loss tan δ of 0.1 at maximum temperature Tm (373° C.). The piezoelectric element had a piezoelectric constant d33* of 293 pm/V and a remnant polarization Pr of 27 µC/cm$^2$, and thus exhibited great piezoelectric properties as a lead-free piezoelectric element. As an indicator for leak current having a great impact on polarization treatment, the dielectric loss tan δ was measured at a temperature of 150° C. and 100 Hz and consequently confirmed to be 0.36, indicating relatively low loss.

Example 2-11

A piezoelectric element was prepared in the same way as in Example 2-10 except that the second heat treatment step and the second cooling step were changed as described below.

<Second Heat Treatment Step (Annealing Step)>

In this Example, the annealing step was carried out in 2 stages (first annealing step and second annealing step) as described below.

(First Annealing Step)

The compact after the second temperature elevation step was annealed at 800° C. for 20 hours in a nitrogen atmosphere.

(Cooling Step)

Next, the compact after the first annealing step was cooled to room temperature at a rate of cooling of 0.01 to 0.05° C./second in a nitrogen atmosphere.

(Temperature Elevation Step)

Next, the temperature of the compact thus cooled was elevated to 500° C. at a rate of temperature rise of 200° C./hr in air.

(Second Annealing Step)

Next, the temperature-elevated compact was annealed at 500° C. for 30 minutes in air.

<Second Cooling Step>

Finally, the compact after the second annealing was cooled to room temperature at a rate of cooling of 200 to 300° C./hr (0.06 to 0.08° C./second) to obtain a piezoelectric composition.

Next, the obtained piezoelectric composition was processed into a thickness of approximately 0.4 mm by polishing and then cut into a size of 4 mm long and 1.5 mm wide. Gold electrodes were formed on both sides of the piezoelectric element by sputtering to obtain a piezoelectric element as illustrated in FIG. 16.

Subsequently, the dielectric properties and piezoelectric properties of the prepared piezoelectric element were measured in the same way as in Example 2-1. As a result, the piezoelectric element had a relative permittivity $\in_r$ of 470 and a dielectric loss tan δ of 0.12 at 25° C. Also, the piezoelectric element had a relative permittivity $\in_m$ of 11,100 and a dielectric loss tan δ of 0.09 at maximum temperature Tm (376° C.). The piezoelectric element had a piezoelectric constant d33* of 309 pm/V and a remnant polarization Pr of 26 μC/cm$^2$, and thus exhibited great piezoelectric properties as a lead-free piezoelectric element. As an indicator for leak current having a great impact on polarization treatment, the dielectric loss tan δ was measured at a temperature of 150° C. and 100 Hz and consequently confirmed to be 0.08 which was lower than ¼ of that of Example 2-10, demonstrating that a piezoelectric element advantageous for polarization can be achieved.

The gas used for the reductive atmosphere in this Example was nitrogen gas. Alternatively, argon gas, nitrogen-hydrogen mixed gas, or the like may be used.

From the results described above, the piezoelectric element prepared by use of the production method of the second aspect involving the heat treatment steps shown in FIG. 18, 19, or 37 can be confirmed to have higher piezoelectric properties or ferroelectric properties than those of a piezoelectric element prepared by a conventional method. Thus, the production method of the second aspect was found very effective for providing a piezoelectric element having high piezoelectric properties or ferroelectric properties with high reproducibility.

As described above, the lead-free piezoelectric element of the second aspect has high piezoelectric properties. Also, the method for producing the lead-free piezoelectric element of the second aspect can conveniently produce, with high reproducibility, a lead-free environment-responsive piezoelectric element containing no lead and having high piezoelectric properties. The lead-free piezoelectric element of the second aspect can be expected to be applied to ultrasonic probes, transducers, sensors, etc. and can be further applied to ultrasonic diagnostic imaging apparatuses.

REFERENCE SIGNS LIST

1 Composition region (excluding segment AE) of the piezoelectric composition of the first aspect
2 More preferred composition region (excluding segment AI) of the piezoelectric composition of the first aspect
3 More preferred composition region (excluding segment JN) of the piezoelectric composition of the first aspect
10, 20, 202 Piezoelectric element
11, 21 Piezoelectric composition
12, 22 Electrode
31 Domain wall
32 Domain
33 Defect
35 Line representing tetragonal-pseudocubic phase boundary
45 Line representing rhombohedral-pseudocubic phase boundary
200, 302 Ultrasonic probe
204 Upper lead electrode
206 Lower lead electrode
220 Back load material
230 First matching layer
232 Second matching layer
240 Acoustic lens
300 Ultrasonic diagnostic imaging apparatus
304 Ultrasonic diagnostic imaging apparatus body
306 Display

The invention claimed is:

1. A piezoelectric composition having a perovskite structure represented by general formula ABO$_3$, and having a composition represented by compositional formula $x(Bi_{0.5}K_{0.5})TiO_3$-$yBi(Mg_{0.5}Ti_{0.5})O_3$-$zBiFeO_3$, wherein x+y+z=1, and also represented by a region, in triangle coordinates using x, y, and z in the compositional formula, enclosed by pentagon ABCDE with vertices of point A (1,0,0), point B (0.7,0.3,0), point C (0.1,0.3,0.6), point D (0.1,0.1,0.8), and point E (0.2,0,0.8) but exclusive of segment AE joining point A (1,0,0) and point E (0.2,0,0.8).

2. The piezoelectric composition according to claim 1, having a composition represented by a region, in the triangle coordinates, enclosed by pentagon AFGHI with vertices of point A (1,0,0), point F (0.8,0.2,0), point G (0.7,0.2,0.1), point H (0.7,0.1,0.2), and point I (0.8,0,0.2) but exclusive of segment AI joining point A (1,0,0) and point I (0.8,0,0.2).

3. The piezoelectric composition according to claim 1, having a composition comprising a tetragonal-pseudocubic phase boundary.

4. The piezoelectric composition according to claim 1, having a composition represented by a region, in the triangle coordinates, enclosed by pentagon JKLMN with vertices of point J (0.6,0,0.4), point K (0.5,0.2,0.3), point L (0.2,0.2, 0.6), point M (0.2,0.1,0.7), and point N (0.3,0,0.7) but exclusive of segment JN joining point J (0.6,0,0.4) and point N (0.3,0,0.7).

5. The piezoelectric composition according to claim 1, having a composition comprising a rhombohedral-pseudocubic phase boundary.

6. The piezoelectric composition according to claim 1, wherein Ti in the compositional formula is partially replaced with Zr.

7. The piezoelectric composition according to claim 1, wherein Bi in the compositional formula is partially replaced with La, Sm, or Nd.

8. The piezoelectric composition according to claim 1, further comprising 2 wt % or less of at least one element selected from the group consisting of Mn, Co, Ni, V, Nb, Ta, W, Si, Ge, Ca, and Sr.

9. A method for producing a piezoelectric composition according to claim 1, comprising:
a starting material preparation step, a temperature elevation step, a heat treatment step, and a cooling step in the order presented.

10. A method for producing a piezoelectric composition according to claim 1, comprising:
a starting material preparation step, a temperature elevation step, a first heat treatment step, a temperature lowering step, a second heat treatment step, and a cooling step in the order presented.

11. A method for producing a piezoelectric composition according to claim 1, comprising:
a starting material preparation step, a first temperature elevation step, a first heat treatment step, a first cooling step, a second temperature elevation step, a second heat treatment step, and a second cooling step in the order presented.

12. A piezoelectric element comprising a piezoelectric composition according to claim 1 and an electrode that applies voltage to the piezoelectric composition.

13. A lead-free piezoelectric element comprising a piezoelectric composition and an electrode that applies voltage to the piezoelectric composition,
the piezoelectric composition having a perovskite structure represented by general compositional formula $ABO_3$ and
comprising $BiFeO_3$ and a Bi complex oxide,
the $BiFeO_3$ having a content of 3 to 80 mol % with respect to the whole piezoelectric composition, and
the Bi complex oxide comprising, in the general compositional formula, Bi at site A and a plurality of elements differing in valence at site B, wherein
the lead-free piezoelectric element has a relative permittivity $\in r$ of 400 or larger and a dielectric loss tan δ of 0.2 or smaller at 25° C., and
has a piezoelectric constant d33* of 250 pm/V or higher determined from an electric field-strain curve.

14. The lead-free piezoelectric element according to claim 13, having a composition comprising a phase boundary between at least 2 types of crystal structures or having a composition located in proximity to the phase boundary.

15. The lead-free piezoelectric element according to claim 14, wherein the phase boundary is a phase boundary between a rhombohedral structure and any one crystal structure selected from the group consisting of pseudocubic, tetragonal, orthorhombic, and monoclinic structures.

16. The lead-free piezoelectric element according to claim 14, wherein the phase boundary is a tetragonal-pseudocubic phase boundary.

17. The lead-free piezoelectric element according to claim 13, wherein the piezoelectric constant d33* is 330 pm/V or higher.

18. The lead-free piezoelectric element according to claim 13, wherein the piezoelectric constant d33* is 360 pm/V or higher.

19. The lead-free piezoelectric element according to claim 13, wherein the $BiFeO_3$ has a content of 30 to 80 mol % with respect to the whole piezoelectric composition.

20. The lead-free piezoelectric element according to claim 13, wherein the piezoelectric composition is made of a relaxor material.

21. The lead-free piezoelectric element according to claim 13, wherein the piezoelectric composition comprises a ceramic having a particle size of 0.5 μm or larger and 200 μm or smaller.

22. The lead-free piezoelectric element according to claim 13, wherein the piezoelectric composition comprises a single crystal.

23. The lead-free piezoelectric element according to claim 13, wherein the piezoelectric composition further comprises $(Bi_{0.5}K_{0.5})TiO_3$ and $Bi(Mg_{0.5}Ti_{0.5})O_3$.

24. The lead-free piezoelectric element according to claim 23, wherein the piezoelectric composition is represented by compositional formula $x(Bi_{0.5}K_{0.5})TiO_3$-$yBi(Mg_{0.5}Ti_{0.5})O_3$-$zBiFeO_3$, where $x+y+z=1$.

25. The lead-free piezoelectric element according to claim 13, wherein the piezoelectric composition further comprises 2 wt % or less of at least one element selected from the group consisting of Mn, Co, Ni, V, Nb, Ta, W, Si, Ge, Ca, and Sr.

26. The lead-free piezoelectric element according to claim 13, having a relative permittivity $\in m$ of 7,000 or larger and a dielectric loss tan δ of 0.2 or smaller at maximum temperature Tm.

27. The lead-free piezoelectric element according to claim 13, having a relative permittivity $\in m$ of 13,000 or larger and a dielectric loss tan δ of 0.2 or smaller at maximum temperature Tm.

28. The lead-free piezoelectric element according to claim 13, having a dielectric loss tan δ of 0.36 or smaller at 150° C. and 100 Hz.

29. The lead-free piezoelectric element according to claim 13, having a dielectric loss tan δ of 0.1 or smaller at 150° C. and 100 Hz.

30. The lead-free piezoelectric element according to claim 26, wherein the maximum temperature Tm is 130° C. or higher and 400° C. or lower.

31. The lead-free piezoelectric element according to claim 13, having a remnant polarization Pr of 20 μC/cm² or larger.

32. An ultrasonic probe comprising a lead-free piezoelectric element according to claim 13.

33. A diagnostic imaging apparatus comprising an ultrasonic probe according to claim 32.

34. A method for producing a lead-free piezoelectric element according to claim 13, comprising a starting material preparation step, a temperature elevation step, a first heat treatment step, a temperature lowering step, a second heat treatment step, and a cooling step in the order presented to produce a piezoelectric composition contained in the lead-free piezoelectric element.

35. The method for producing a lead-free piezoelectric element according to claim 34, wherein the heat treatment temperature of the first heat treatment step is 800 to 1,150° C.

36. The method for producing a lead-free piezoelectric element according to claim 34, wherein the heat treatment time of the first heat treatment step is 2 to 300 hours.

37. The method for producing a lead-free piezoelectric element according to claim 34, wherein the heat treatment time of the first heat treatment step is 2 to 3,000 hours.

38. The method for producing a lead-free piezoelectric element according to claim 34, wherein the heat treatment temperature of the second heat treatment step is 300 to 900° C.

39. The method for producing a lead-free piezoelectric element according to claim 34, wherein the heat treatment time of the second heat treatment step is 5 minutes to 100 hours.

40. The method for producing a lead-free piezoelectric element according to claim 34, wherein the second heat treatment step is carried out in two or more rounds at different temperatures.

41. The method for producing a lead-free piezoelectric element according to claim 40, wherein the different temperatures are 600 to 900° C. on the high temperature side and 300 to 600° C. on the low temperature side.

42. The method for producing a lead-free piezoelectric element according to claim 34, wherein the rate of cooling in the cooling step is 0.01 to 200° C./second.

43. A method for producing a lead-free piezoelectric element according to claim 13, comprising a starting material preparation step, a first temperature elevation step, a first heat treatment step, a first cooling step, a second temperature elevation step, a second heat treatment step, and a second cooling step in the order presented to produce a piezoelectric composition contained in the lead-free piezoelectric element.

44. The method for producing a lead-free piezoelectric element according to claim 43, wherein the heat treatment temperature of the first heat treatment step is 800 to 1,150° C.

45. The method for producing a lead-free piezoelectric element according to claim 43, wherein the heat treatment time of the first heat treatment step is 2 to 300 hours.

46. The method for producing a lead-free piezoelectric element according to claim 43, wherein the heat treatment time of the first heat treatment step is 2 to 3,000 hours.

47. The method for producing a lead-free piezoelectric element according to claim 43, wherein the heat treatment temperature of the second heat treatment step is 300 to 900° C.

48. The method for producing a lead-free piezoelectric element according to claim 43, wherein the heat treatment time of the second heat treatment step is 5 minutes to 100 hours.

49. The method for producing a lead-free piezoelectric element according to claim 43, wherein the second heat treatment step is carried out in two or more rounds at different temperatures.

50. The method for producing a lead-free piezoelectric element according to claim 49, wherein the different temperatures are 600 to 900° C. on the high temperature side and 300 to 600° C. on the low temperature side.

51. The method for producing a lead-free piezoelectric element according to claim 43, wherein the rate of cooling in the second cooling step is 0.01 to 200° C./second.

52. The method for producing a lead-free piezoelectric element according to claim 43, further comprising a processing step for the piezoelectric composition between the first cooling step and the second temperature elevation step.

53. The method for producing a lead-free piezoelectric element according to claim 52, further comprising an electrode preparation step after the processing step.

* * * * *